US012797065B2

(12) United States Patent
Thissen et al.

(10) Patent No.: US 12,797,065 B2
(45) Date of Patent: Nov. 17, 2026

(54) SUTURING SYSTEM AND STAPLES

(71) Applicant: Bastion Labworks LLC, West Palm Beach, FL (US)

(72) Inventors: Frank Thissen, Manahawkin, NJ (US); Juan E. Vega-Nevarez, Jersey City, NJ (US)

(73) Assignee: Bastion Labworks LLC, West Palm Beach, FL (US)

(*) Notice: Subject to any disclaimer, the term of this patent is extended or adjusted under 35 U.S.C. 154(b) by 0 days.

(21) Appl. No.: 19/224,649

(22) Filed: May 30, 2025

(65) Prior Publication Data

US 2025/0366848 A1 Dec. 4, 2025

Related U.S. Application Data

(60) Provisional application No. 63/721,358, filed on Nov. 15, 2024, provisional application No. 63/654,344, filed on May 31, 2024.

(51) Int. Cl.
*A61B 17/04* (2006.01)
*A61B 17/00* (2006.01)
(Continued)

(52) U.S. Cl.
CPC .... *A61B 17/0482* (2013.01); *A61B 17/06166* (2013.01); *A61B 17/064* (2013.01); *A61B 17/0682* (2013.01); *A61B 17/07207* (2013.01); *A61B 2017/00004* (2013.01); *A61B 2017/00367* (2013.01); *A61B 2017/00867* (2013.01);
(Continued)

(58) Field of Classification Search
CPC .............. A61B 17/064; A61B 17/0682; A61B 17/0482; A61B 17/072; A61B 17/1152; A61B 2017/1157
See application file for complete search history.

(56) References Cited

U.S. PATENT DOCUMENTS

| | | | |
|---|---|---|---|
| 3,795,034 | A | 3/1974 | Strekopytov et al. |
| 4,747,358 | A | 5/1988 | Moll et al. |

(Continued)

FOREIGN PATENT DOCUMENTS

| | | | |
|---|---|---|---|
| CN | 109310417 | A | 2/2019 |
| EP | 0599772 | A1 | 6/1994 |
| WO | 2022166118 | A1 | 8/2022 |

OTHER PUBLICATIONS

"Quill—The Barbed Suture Pioneer"; Website: https://www.premiersurgical.ie/orthopaedic/quill/; retrieved Oct. 27, 2025; Copyright 2019 Premier Surgical; 8 pages.

(Continued)

*Primary Examiner* — Mohamed G Gabr
*Assistant Examiner* — Khoa Tan Le
(74) *Attorney, Agent, or Firm* — Greenberg Traurig, LLP; Roman Fayerberg; David J. Dykeman

(57) ABSTRACT

A suturing system includes a suturing device that includes a staple and a staple drive. The staple includes a center portion and end portions extending from the center portion. The end portions have hollow interiors terminating at end openings and are configured to removably receive portions of a suture segment. The staple drive is coupled to the staple to impel the staple containing the suture segment into tissue and to retract the staple from the tissue while leaving the suture segment in the tissue.

19 Claims, 25 Drawing Sheets

(51) Int. Cl.

| | |
|---|---|
| ***A61B 17/06*** | (2006.01) |
| ***A61B 17/064*** | (2006.01) |
| ***A61B 17/068*** | (2006.01) |
| ***A61B 17/072*** | (2006.01) |

(52) U.S. Cl.

CPC ............... *A61B 2017/06176* (2013.01); *A61B 2017/0618* (2013.01)

(56) References Cited

U.S. PATENT DOCUMENTS

| | | | |
|---|---|---|---|
| 4,944,443 | A | 7/1990 | Oddsen et al. |
| 5,496,334 | A | 3/1996 | Klundt et al. |
| 5,630,540 | A | 5/1997 | Blewett |
| 6,270,517 | B1 | 8/2001 | Brotz |
| 6,616,686 | B2 | 9/2003 | Coleman et al. |
| 8,246,652 | B2 | 8/2012 | Ruff |
| 8,435,254 | B2 | 5/2013 | Kostrzewski |
| 8,888,810 | B2 | 11/2014 | Hadba et al. |
| 9,113,863 | B2 | 8/2015 | Kostrzewski |
| 2002/0169465 | A1 | 11/2002 | Bowman et al. |
| 2004/0092963 | A1 | 5/2004 | Moll et al. |
| 2004/0122471 | A1 | 6/2004 | Toby et al. |
| 2009/0182375 | A1 | 7/2009 | Isse et al. |
| 2009/0234373 | A1 | 9/2009 | Frings et al. |
| 2011/0226837 | A1 | 9/2011 | Baxter, III et al. |
| 2012/0116448 | A1 | 5/2012 | Reiffel |
| 2012/0271325 | A1 | 10/2012 | Yoon |
| 2013/0289584 | A1 | 10/2013 | Bender et al. |
| 2015/0238190 | A1 | 8/2015 | Euteneuer |
| 2017/0281163 | A1 | 10/2017 | Shelton et al. |
| 2021/0169465 | A1 | 6/2021 | Chalekson et al. |
| 2021/0275290 | A1* | 9/2021 | Domecus .............. A61F 2/0811 |

OTHER PUBLICATIONS

Gowri et al.; "A Review of Barbed Sutures-Evolution, Applications and Clinical Significance"; Bioengineering 2023, 10, 419; Mar. 27, 2023; Basel, Switzerland; 19 pages.

International Search Report and Written Opinion for PCT/US2025/031821; mail date Jul. 24, 2025; 10 pages.

International Search Report and Written Opinion for PCT/US2025-031823; mail date Jul. 25, 2025; 8 pages.

Sannohe et al., Single Layer Suture By Manual Or Mechanical Stapling Technique In Esophagojejunostomy After Total Gastrectomy, The American Journal of Surgery, vol. 142, Issue 3, pp. 403-406, Sep. 1981.

* cited by examiner

SUTURING SYSTEM AND STAPLES

CROSS-REFERENCE TO RELATED PATENT APPLICATIONS

This application claims the benefit of U.S. Provisional Application No. 63/654,344 filed May 31, 2024, entitled SUTURING SYSTEM, and claims the benefit of U.S. Provisional Application No. 63/721,358, filed Nov. 15, 2024, entitled SUTURING SYSTEM, both of which are incorporated herein in their entireties. The present application is related to co-pending U.S. patent application Ser. No. 19/224,654 filed on May 30, 2025, by Thissen et al. and entitled SUTURING SYSTEM WITH PRESSURE FOOT, the full disclosure of which is hereby incorporated by reference.

BACKGROUND

Suturing is used to join tissue to facilitate healing.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

BRIEF DESCRIPTION OF THE DRAWINGS

FIGS. 33A and 33B illustrate an example method for bending a wire.

FIG. 34D is a first view illustrating the assembled staple of FIG. 34A.

Figure 1:
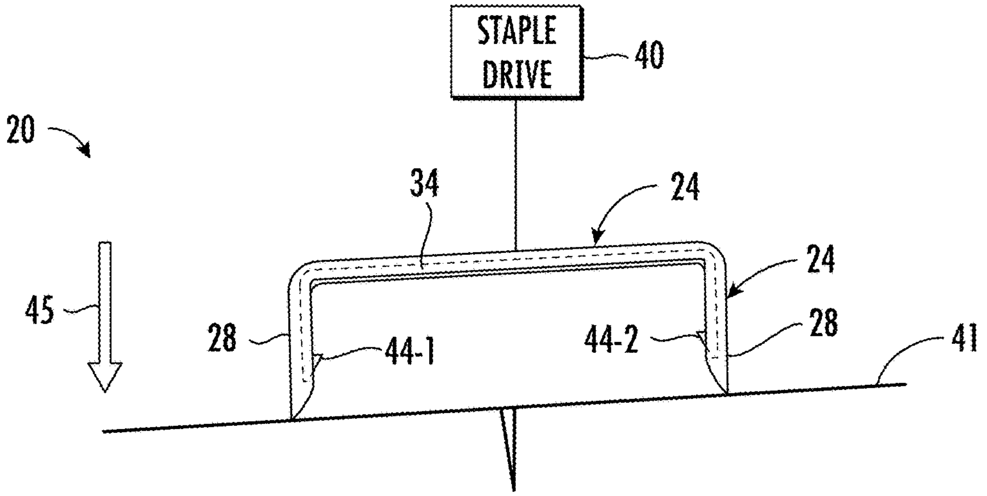
FIG. 1 is a diagram schematically illustrating portions of an example suturing system.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed are suturing systems that achieve concurrent implantation of multiple suture segments across a tissue break or wound opening. Such implantation results in opposite end portions of multiple suture segments being concurrently implanted in tissue on opposite sides of the tissue break or wound opening with central portions of such suture segments extending at or near the surface of the tissue, spanning across the tissue break. The disclosed suturing systems are portable, configured for being handheld and manually manipulated. The disclosed suturing systems are lightweight, have a low level of complexity, and are low cost. Each of such systems may be operated using manually applied force, avoiding the need for batteries or other electrical power sources. In some implementations, each of such systems may include a powered actuator for implanting the suture segments. Each of such systems may be utilized as part of a robotic surgical system. For example, each of such systems may be provided on or incorporated into the end of a robotic arm as an end effector. The disclosed suturing systems provide fast, efficient, reliable and steadfast implantation of a suture across a tissue break or wound opening.

For purposes of this disclosure, the term “coupled” shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such a joining may be permanent in nature or alternatively may be removable or releasable in nature. The term “operably coupled” shall mean that two members are directly or indirectly joined such that motion may be transmitted from one member to the other member directly or via intermediate members.

For purposes of this disclosure, the phrase “configured to” denotes an actual state of configuration that fundamentally ties the stated function/use to the physical characteristics of the feature proceeding the phrase “configured to”.

For purposes of this disclosure, the term “releasably” or “removably” with respect to an attachment or coupling of two structures means that the two structures may be repeatedly connected and disconnected to and from one another without material damage to either of the two structures or their functioning.

The following disclosure describes suture segments to be implanted. Each of the disclosed suture segments may be biodegradable. For purposes of this disclosure, “biodegradable” means that the segment is dissolvable within the natural fluids found within the human body. For example, in some implementations, the suture segments are dissolvable within a time period of 90 to 120 days, in some implementations 210 days and, in other implementations, other periods of time per application requirements, in the natural fluids that exist within the human body. In such implementations, connectors 448 may likewise be formed from the same or a different composition that is biodegradable and such or dissolvable within a time period of 90-120 days, or 210 days, depending on use case. Some materials may dissolve in weeks instead of months. within the natural fluids found within the human body.

Figure 2:
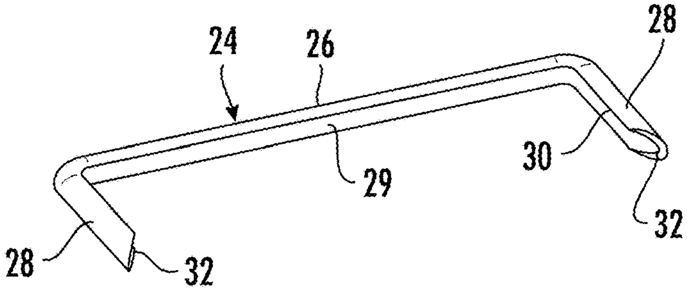
FIG. 2 is a perspective view of an example staple of the suturing system of FIG. 1.
Figure 3:
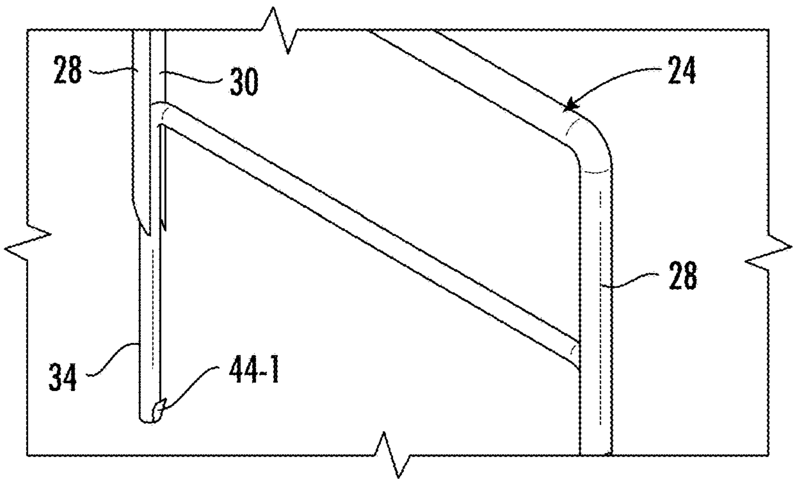
FIG. 3 is a perspective view illustrating positioning of a suture segment into the example staple of FIG. 2.

FIGS. 1-5 illustrate portions of an example suturing system 20. System 20 comprises staple 24, and staple drive 40. As shown by FIGS. 1-3, staple 24 comprising a center portion 26 and end portions 28 extending from the center portion 26. As seen in FIGS. 2 and 3, the end portions 28 comprise hollow interiors 30 having inwardly mutually facing slots or side openings forming and terminating at end openings 32 such that the end portions 28 are configured to removably receive portions of a suture segment 34. In the example illustrated, center portion 26 further comprises a hollow interior 29 with a downwardly facing slot opening which is continuous with the hollow interiors 30 and the side openings of end portions 28. As result, a majority, if not all of the longitudinal length of suture segment 34 may be received or captured within hollow interiors 29 and 30 prior to the insertion or impelling of the suture segment 34 into tissue being sutured. In some implementations, center portion 26 may omit a hollow interior or only a portion of its length may have a hollow interior with a downwardly facing slot or side opening.

In the example illustrated, end openings 32 are tapered or pointed to facilitate penetration into tissue being sutured. In the example illustrated, at least end portions 28 are sufficiently rigid or unbendable so as to penetrate the underlying tissue being sutured. In some implementations, center portion 26 is likewise sufficiently rigid to maintain shape as end portions 28 penetrate the underlying tissue. In some implementations, staple 24 may be formed from a metal, such as stainless steel. In other implementations, staple 24 may be formed from other materials.

Figure 4:
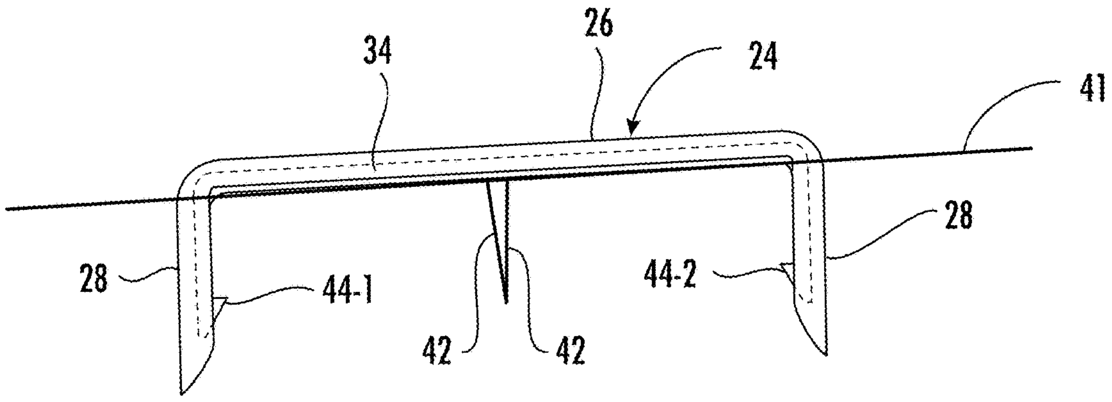
FIG. 4 is a diagram illustrating implantation of a suture segment by the suturing system of FIG. 1.
Figure 5:
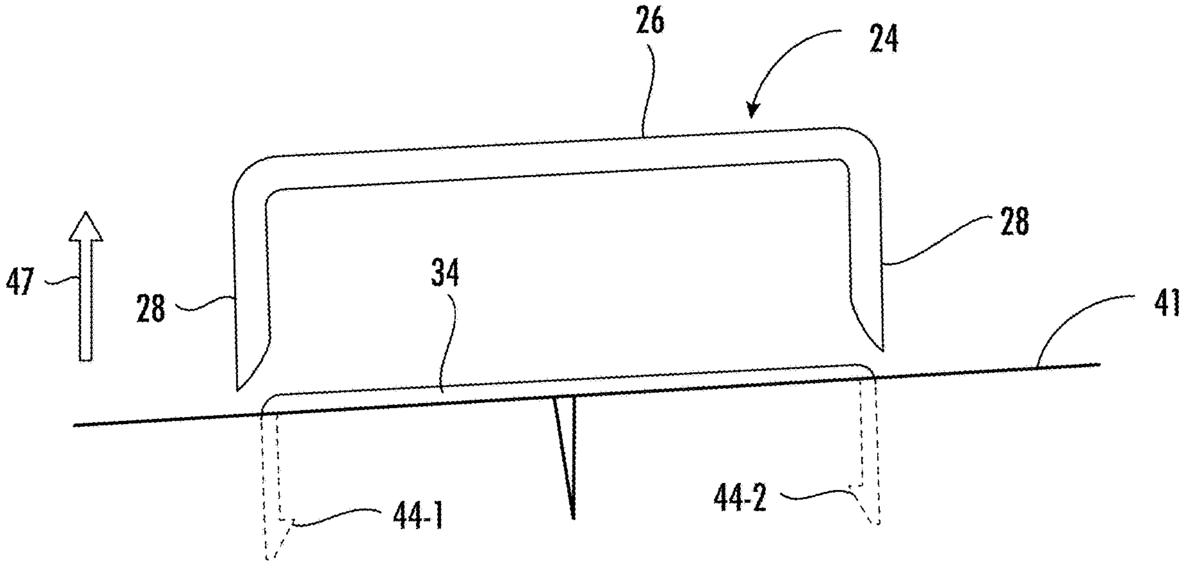
FIG. 5 is a diagram illustrating removal of the staple of FIG. 2 following implantation of the suture segment.

Suture segment 34 comprises a flexible line having a first enlarged portion 44-1 proximate to a first end and a second enlarged portion 44-2 proximate to a second end. In the example illustrated, the enlarged portions 44-1 and 44-2 each comprises a barb. Such barbs are schematically illustrated in FIGS. 1, 4 and 5. As schematically illustrated, each of such barbs 44 has pointed tips and at least one widened rear portion to the facilitate penetration into tissue 41 but resist withdrawal of the inserted suture segment 34 from the tissue 41.

In some implementations, the flexible line providing suture segment 34 may comprise multiple spaced barbs. In some implementations, the flexible line providing suture segment 34 may comprise a series of spaced barbs along its entire longitudinal length. For example, the flexible line may have a first plurality of barbs on a first side of and pointing away from a longitudinal center of the flexible line and a second plurality of barbs on a second side of and pointing away from the longitudinal center of the flexible line.

In some implementations, the flexible line forming suture segment 34 has shape memory. In some implementations, the flexible line comprises portions that are elastic, wherein the suture segment 34 may be stretched during penetration and insertion into the underlying tissue, wherein the suture segment will subsequently retract once in the tissue to draw together opposite edge portions of the cut or incision being sutured. In some implementations, the suture segment 34 is formed from an organ absorbable and dissolvable material, such as Polydioxanone (PDS), eliminating the need to subsequently remove the suture. In some implementations, the suture segment 34 has a length of at least 9 mm and no greater than 15 mm. In some implementations, the flexible line forming suture segment 34 has a diameter or thickness of at least 3-0 (United States Pharmacopeia (USP) numbering system for sutures, (0.25 mm) and no greater than 1 USP (0.4 mm).

Staple drive 40 comprises a mechanism configured to be coupled to the staple 24 to impel the staple 24 containing the suture segment 34 into tissue 41 across the separated edges 42 of the tissue 41 being sutured. Staple drive 40 is further configured to retract the staple 24 from the tissue 41 while leaving the suture segment 34 in the tissue 41. Staple drive 40 may comprise a hydraulic, pneumatic or another mechanism operably coupled to center portion 26 so as to exert force against center portion 26 to impel tissue 41 with end portions 28 and may likewise exerting opposite force against center portion 26 so as to withdraw staple 24 from the tissue. In some implementations, staple drive 40 may utilize manual force to impel the staple 24 and manual force to withdraw staple 24. In some implementations, staple drive 40 may utilize one or more springs for driving staple 24 into tissue 41 and/or for withdrawing staple 24 from tissue 41. The actuation of staple drive 40 or the triggering of staple drive 40 may be in response to a manual input to staple drive 40.

FIGS. 1, 4 and 5 illustrate the application of an individual suture segment 34 across the opposite separated tissue edges 42 of tissue 41 being sutured. As shown by FIG. 1, prior to suture segment 34 being impelled into tissue 41, suture segment 34 may be contained within the hollow interiors 29, 30 of staple 24. As shown by FIG. 4, suture segment 34 remains within the hollow interiors 29, 30 of staple 24 during movement of staple 24 in the direction indicated by arrow 45 in FIG. 1 until staple 24 is fully penetrated tissue 41. As shown by FIG. 5, following such penetration, staple 24 may be withdrawn from tissue 41 by staple drive 40 in the direction indicated by arrow 47. During such withdrawal of staple 24, barbs 44-1 and 44-2 resist withdrawal, maintaining the penetrated state of suture segment 34. Thereafter, staple 24 may receive a new suture segment 34 and staple drive 40 may be actuated to drive another suture segment 34 at another position across the opposite edges 42 of the tissue 41 being sutured.

Figure 6:
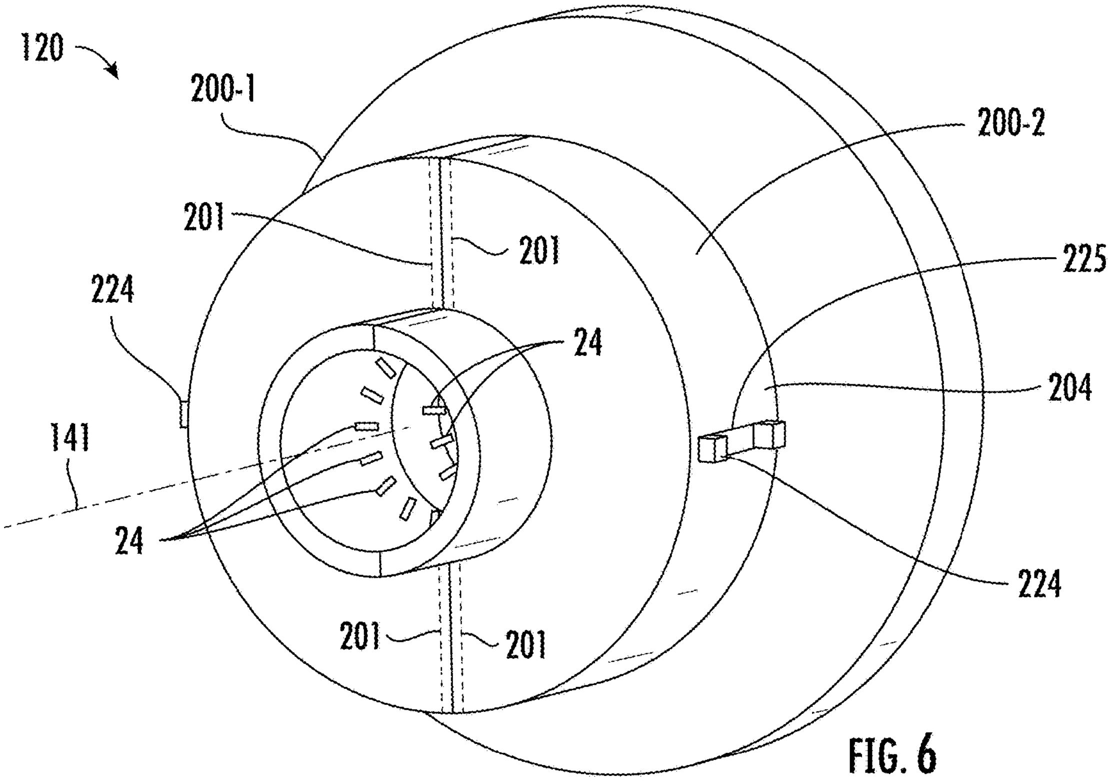
FIG. 6 is a perspective view of an example suturing system.
Figure 7:
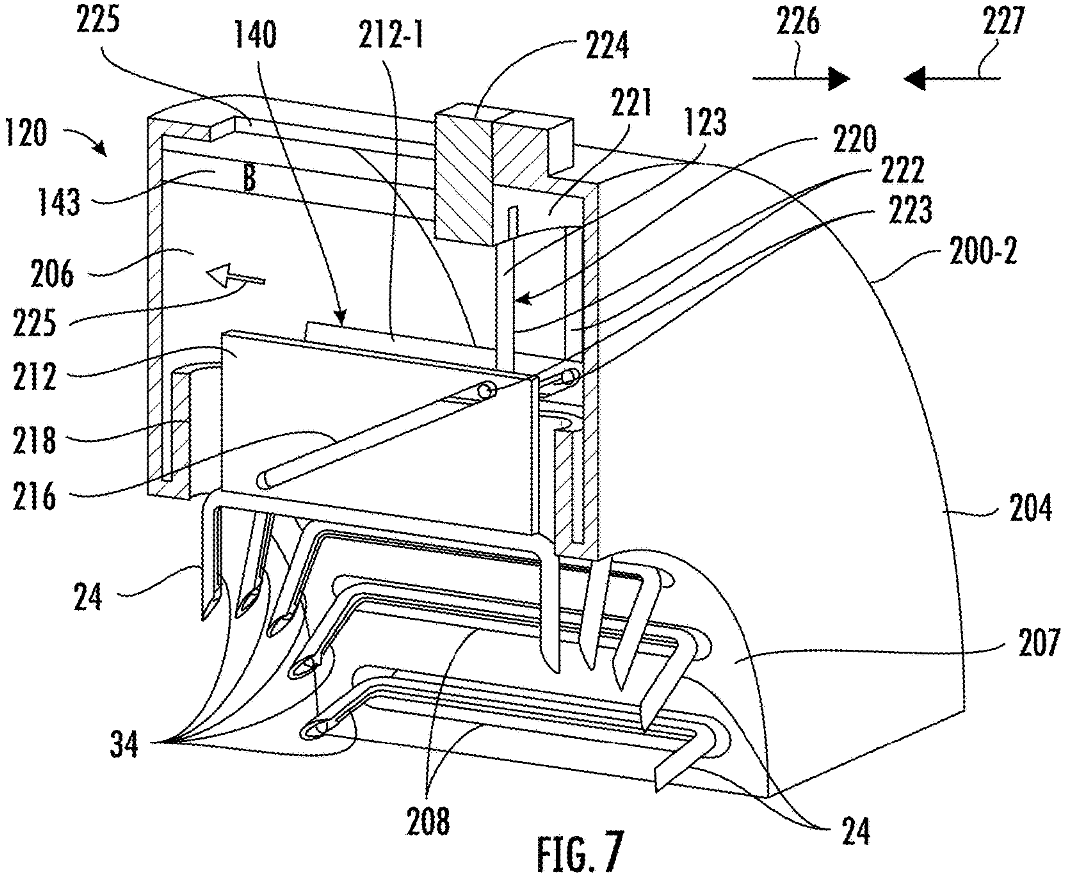
FIG. 7 is a sectional view of the suturing system of FIG. 6.

FIGS. 6 and 7 illustrate an example suturing system 120. System 120 configured to simultaneously or concurrently impel underlying tissue with a plurality of suture segments, such as suture segment 34. In the example illustrated, suture system 120 concurrently or simultaneously impels a plurality of suture segments in radial directions about an axis. As result, system 120 may be well suited for surgical procedures such as anastomosis, the surgical connection between two tubular structures.

As shown by FIG. 6, system 120 comprises a staple drive 140 having two clamshell halves 200-1 and 200-2 (collectively referred to as halves 200) which may be positioned about opposite sides of a tubular organ to be sutured. The clamshell configuration facilitates the positioning of system 120 about tubular anatomical structures to be joined without having to slide system 120 over end of the two tubular anatomical structures. The halves 200 mate about a centerline 141. The staple drive 140 is configured to concurrently support a plurality of staples 24 360 degrees around the centerline 141. The staple drive 140 is configured to concurrently drive each of the plurality of staples 24 into the tissue towards the centerline 141 and concurrently retract each of the plurality of staples 24 from the tissue, leaving a plurality of suture segments 34 within the tissue, 360 degrees about the two tubular organ or anatomical structures being sutured. As a result, system 120 may be used to join two separated or partially severed portions of a tubular anatomical structure.

In the example illustrated, each of halves 200 are identical and mirror one another. In some implementations, the halves 200 are releasably secured to one another by magnets 201 (schematically illustrated). In other implementations, the two halves 200 may be releasably secured to one another by fasteners, or other attachment or securement mechanisms. In some implementations, the two halves may be joined by a hinge such as a mechanical hinge or a living hinge.

FIG. 7 is a sectional view illustrating a clamshell portion of half 200-2. FIG. 7 Illustrates staple drive construction for driving a staple containing a suture segment into tissue to be sutured (similar to the process shown in FIGS. 1 and 4-5). As shown by FIG. 7, half 200-2 comprises an arcuate housing 204 configured to partially extend about the longitudinal axis of the tubular organ to be sutured. Housing 204 comprises an interior 206 containing staple drive 140 in a series of circumferentially spaced radial slots 208 through which corresponding staples 24 may be concurrently driven by staple drive 140. Prior to being impelled into the tissue being sutured, each of such staples 24 may be retracted into interior 206 such that the inner circumferential surface 207 of housing 204 may be positioned into close proximity or contact with the tissue being sutured.

Staple drive 140 comprises a series of slotted members 212, drive member 220 and actuation interface 224. Slotted members comprise members, such as plates, which are secured to a top or outer side of central portion 26 of respective staples 24. Each slotted member 212 comprises an angularly extending slot 216 and is slidably supported within a track or other guiding structure 218 provided by housing 204.

Drive member 220 is slidably received within each of slots 216 of each of slotted members 212. Drive member 220 comprises a semi-annular inner ring 221 and cam rods 222. Inner ring 221 comprises an annular sleeve or tube which axially slides along centerline 141, bearing against the inner circumferential surface of housing 204, Cam rods 222 are connected to inner ring 221 and radially extend inwards towards respective slotted members 212. Each cam rods 222 has an angled end 223 slidably received within a respective slot 216. The movement of ends 223 of drive member 220 within the respective slots 216 radially moves slotted members 212 and the associated staples 24 radially towards the centerline 141 about which housing 204 extends.

Actuation interface 224 comprise a mechanism configured to move ring 221 of drive member 220 along centerline 141 to concurrently move all of cam rods 223 and their ends 223 to concurrently move slotted members 212 and staples 2245. In the example illustrated, actuation interface 224 comprises a button or bar that is manually moved within a guiding channel 225 provided in an exterior wall of housing 204. Movement of interface 224 in the direction indicated by arrow 226 concurrently drives the multiple staples 24 in a radial direction into the tissue being sutured. Conversely, movement interface 224 in the direction indicated by arrow 227 radially withdraws staples 24 from the tissue being sutured.

In the example illustrated in which system 120 comprises clamshell halves 200, application of suture segments 24 may be carried out by movement of the interface 224 of each of the halves 200. System 120 concurrently implants suture segments 24 at least 180° about the centerline 141 of a tubular anatomical structure. For example, during a radical prostatectomy, the tubular anatomical structure between the bladder and the prostate is cut, the cancerous prostate is removed and the tubes previously existing on opposite sides of the prostate are subsequently directly connected to one another by sutures. In such an application, upon removal of the prostate, system 120 may be positioned about opposite sides of or axially across the two separate tubular anatomical structures (originally existing on opposite sides of the prostate) such that multiple suture segments may be concurrently implanted at least 180° about the centerline of the two separate but abutting or partially overlapping the anatomical structures being joined. The actuation of interfaces 224 of the two halves 200 to implant the suture segments 24 may be performed concurrently or sequentially. Concurrent actuation of the two interfaces 224 facilitate concurrent application of segments 24 360° about the centerline 141 of the anatomical structure being sutured. Sequential actuation of the two interface 224 results in a first instance wherein suture segments 24 are implanted a first 180 degrees about the centerline 141 and a second instance wherein suture segments 24 are applied about a second 180° about the centerline 141. System 120 may be similarly used in other surgical procedures.

In some implementations, the joining of the two halves 200 may result in mechanical or magnetic connection of the axial ends of the two rings 221 of the two halves 200 such that movement of one of the rings 221 results in corresponding movement of the other of rings 221 of the two halves 200. For example, the mutually facing and abutting faces of the rings of both halves 200 along the junction of halves 200 may be formed from permanent magnets (or a permanent magnet and a ferrous material) such that the two rings magnetically stick to one another when the halves 200 are brought together about the tubular anatomical structure being sutured. In such an implementation, axial movement of a first one of the interfaces 224 results in corresponding movement its associated first ring 221 and corresponding movement of the second ring 221 of the other half 200 (magnetically held and joined top the first ring) such that all of the cam rods 222 of both halves 200 are moved to drive all of the staples 24 to concurrently implant suture segments 34 360 degrees about the centerline 141. In some implementations, a first one of the two halves 200 may omit its interface 224, relying upon movement the actuation interface 224 of the second one of the halves 200 for driving of it staples 24.

In some implementations, system 120 may additionally include a bias mechanism 143 (such as a tension spring, schematically illustrated) to resiliently bias actuation interface 224 in the direction indicated by arrow 225 towards a staple retracted position in which each of staples 24 is retracted through slots 208 into housing 204, wherein movement of interface 224 in the opposite direction, toward the illustrated staple impelling or implanting position, against the bias force of the spring 143, impels the tissue with the staples 24. In some implementations, other bias mechanisms, such as leaf springs or tension springs may be used to bias interface 224 to the position in which each of staples 24 is retracted through slots 208 into housing 204.

Figure 8:
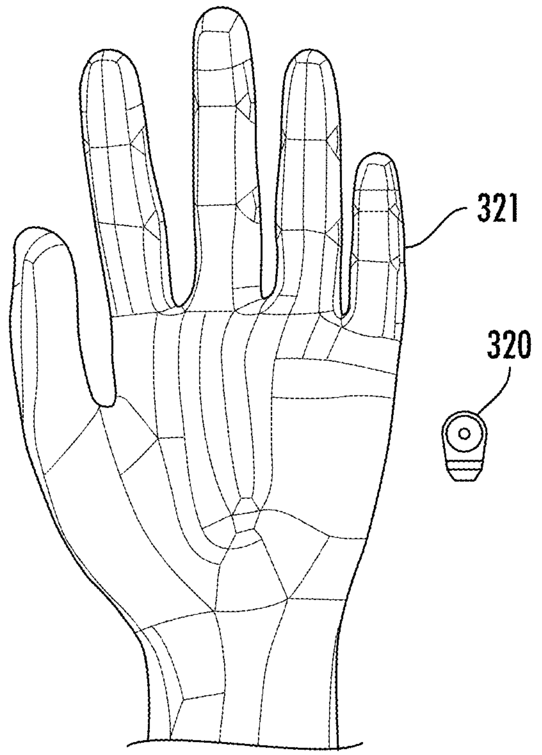
FIG. 8 is a perspective view of an example suturing system proximate an average male human hand.

FIGS. 8-26 illustrate portions of an example suturing system 320. FIG. 8 illustrates one example implementations suturing system 320 having the illustrated scale with respect to an average human hand. As result, suturing system 320 may be well suited for suturing tissue of internal organs with reduced incision opening sizes. In some implementations, suturing system 320 may be provided are carried by a finger attachment, such as a ring or fingertip by which a surgeon may repeatedly manually actuate suturing system 320 place a series of suture segments across a split or adjacent/obstacle to the tissue being sutured.

FIG. 8 illustrates and example suturing system 320 positioned next to an average male human hand 321. As shown by FIG. 8, system 320 may be held between one's thumb and index finger while being positioned in tight anatomical spaces while being manipulated to implant a suture. In other implementations, system 320 may have other sizes.

Figure 9:
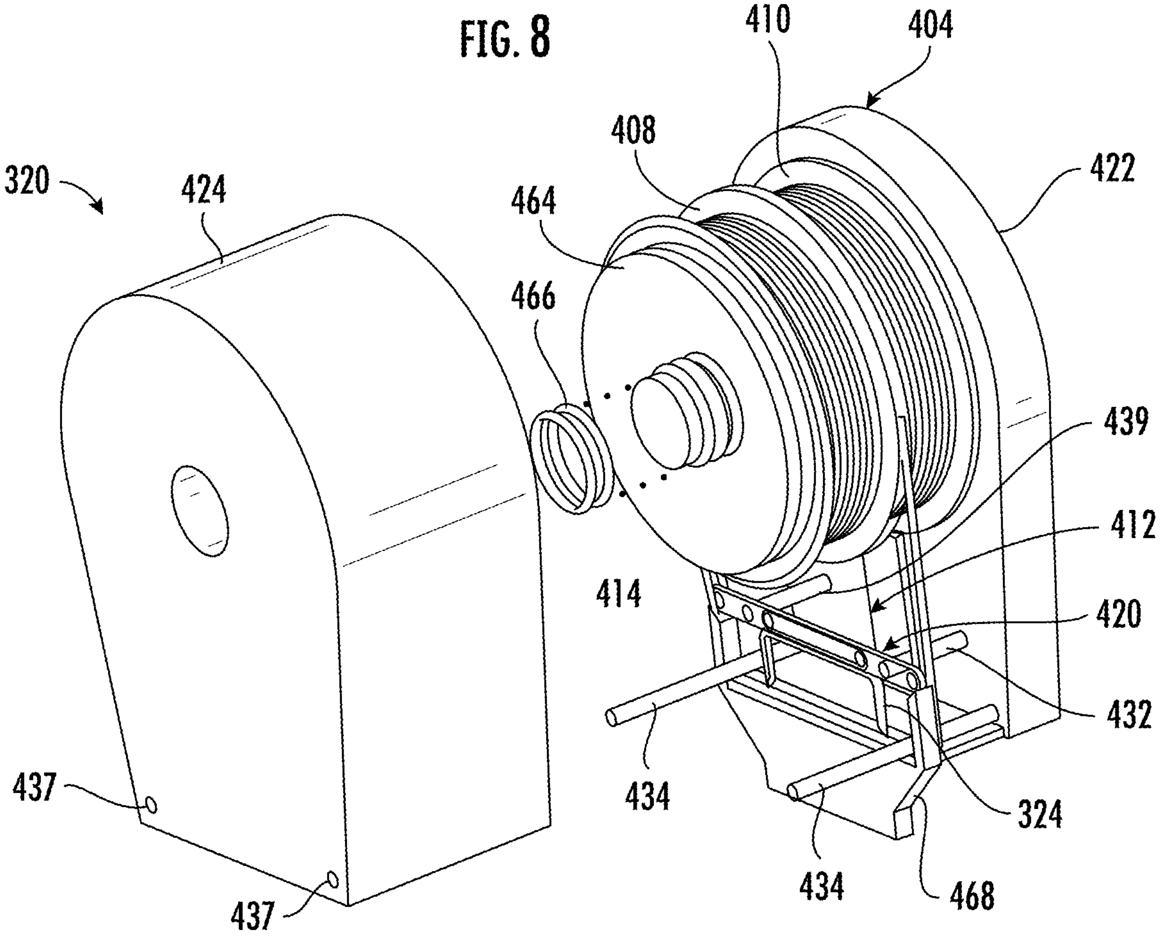
FIG. 9 is a partially exploded perspective view of the suturing system of FIG. 8.

FIG. 9 is an enlarged perspective view of system 320. As shown by FIG. 9, suturing system 320 comprises housing 404, supply reel 408, take-up reel 410, suture supply line 414, staple 324 (similar to staple 24 described above), line feeder 412 and staple drive 420. Housing 404 comprises structure supporting and enclosing components of system 320. In the example illustrated, housing 404 comprises a support portion 422 and a cover 424. Cover 424 joined support portion 422 to enclose the remaining components of system 320.

Figure 10:
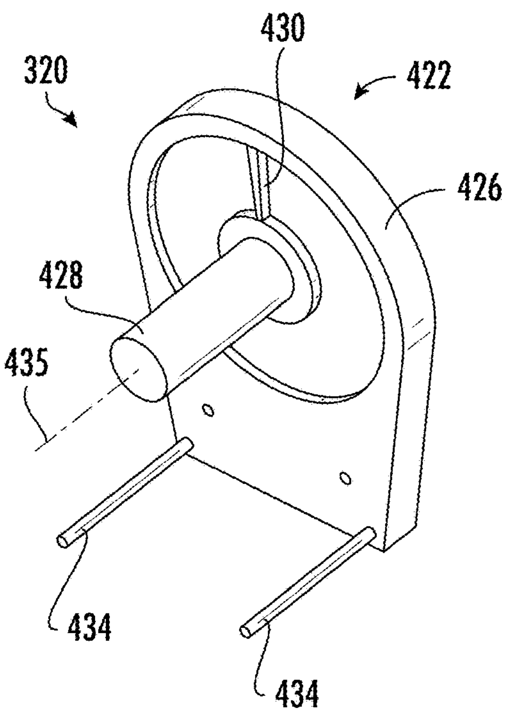
FIG. 10 is a perspective view illustrating a portion of the suturing system of FIG. 9.
Figure 11:
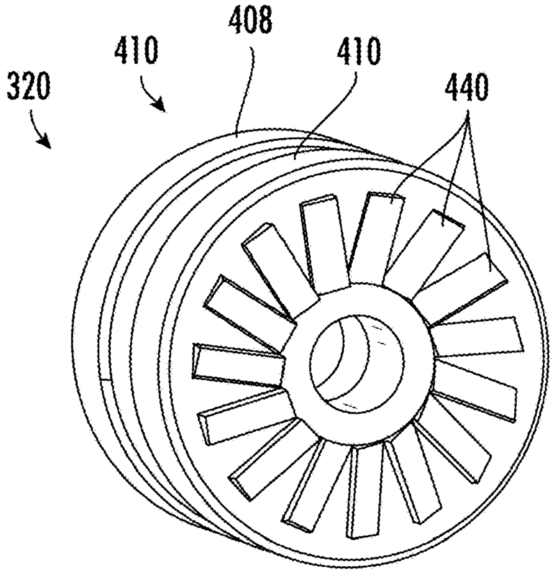
FIG. 11 is a perspective view illustrating a portion of the suturing system of FIG. 9.

FIG. 10 illustrates support portion 422 separated from the remainder of system 320. Support portion 422 comprises wall 426, axle 428, catch 430, pivot rods 432 (shown in FIG. 9) and guide rods 434. Axle 428 serves as a spindle and projects from wall 426 to rotatably support feed reel 408 and take-up reel 410 for rotation about axis 435. Catch 430 comprises a projection or protuberance extending from wall 426 for engaging ratchet teeth 440 provided on a rear face of take-up reel 410 as shown in FIG. 11. Catch 430 and ratchet teeth 440 are part of line feeder 412.

Pivot rods 432 (shown in FIG. 9) project from wall 426 and pivotably support portions of staple drive 420. Guide rods 434 project from wall 426 and are received within openings 437 to secure cover 424 (shown in FIG. 9). Guide rods 434 further guide and stretch suture supply line 414 opposite to and across staple 324.

Suture feed reel 408 comprise a spool containing a supply of suture supply line 414 wound about the spool. Take-up reel 410 comprise a spool for winding and receiving used portions of suture supply line 414 (those portions from which suture segments have been separated and removed). In the example illustrated, reels 408 and 410 are fixed to one another so as to rotate in unison with one another.

Figure 12:
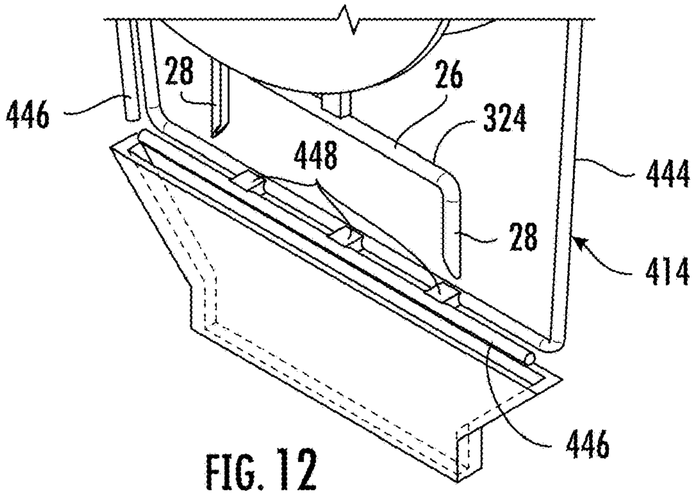
FIG. 12 is a perspective view illustrating portions of the example suturing system of FIG. 9.

FIG. 12 illustrates suture supply line 414 being guided and stretched across staple 324 by guide rods 434 (which are hidden or not shown for purposes of illustration). As shown by FIG. 12, suture supply line 414 comprises a carrier line 444 and a series of suture segments 446. Each of suture segments 446 is carried by carrier line 444 and is separable from carrier line 444. In the example illustrated, each of suture segment 446 is connected to carrier line 444 by one or more segment connectors 448. Segment connectors 448 are configured such that segments 446 break away from connectors 448 in response to sufficient forces exerted against an individual segment 446 by staple 324. In the example illustrated, connector 448 may further break away from the associated segment 446. In other implementations, connectors 448 may remain connected to carrier line 444 following separation from their respective segments 446.

In some implementations, carrier line 444 has a first material composition while each of segments 446 has a different material composition. In some implementations, each of segments 446 may be formed from a composition that is biodegradable and/or dissolvable within a time period of 90 to 120 days, in some implementations 210 days and in other implementations, other periods of time per application requirements, in the natural fluids that exist within the human body. In such implementations, connectors 448 may likewise be formed from the same or a different composition that is biodegradable and such or dissolvable within a time period of 90-120 days, or 210 days, depending on use case. Some materials may dissolve in weeks instead of months. within the natural fluids found within the human body. In such implementations, carrier line 444 may be formed from the same material or may be formed from a composition that is not biodegradable and/are not dissolvable in response to exposure to natural fluids found within the human body for the noted time period. In one example implementation, carrier line 444 is formed from a material such as silk while each of suture segments 446 and connectors 448 are formed from material such as Polydioxanone (PDS). As noted above, supply or feed reel 408 contains a winding or supply of line 414 including both carrier line 444 and the attached segments 446. Take-up reel 410 receives or whines those portions of carrier line 444 that no longer carry segments 446, after segments 446 have been stripped from carrier line 444 by actuation of staple 324.

Figure 13:
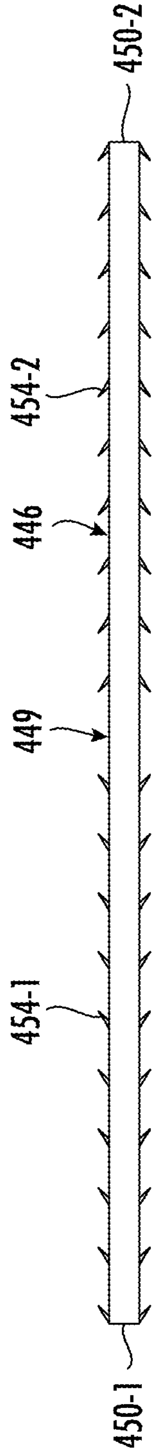
FIG. 13 is a perspective view illustrating an example suture segment.

In some implementations, each of segments 446 may be similar to 734 described above. In other implementations, each of segments 446 may have other configurations. FIG. 13 illustrates an individual suture segment 446 separated from carrier line 444 and prior to bending of segment 446 by staple 324. Suture segment 446 comprises an elongate flexible line having a center 449 and opposite ends 450-1, 450-2 (collectively referred to as ends 450). As shown by FIG. 13, segment 446 comprises a first series of barbs 454-1 and a second series of barbs 454-2 (collectively referred to as barbs 454). Barbs 454-1 point towards end 450-1 and extends generally from center 449 to end 450-1. Barbs 454-2 point towards and 450-2 and extend generally from center 449. Barbs 454 outwardly and angularly project away from the centerline of segments 446 on opposite sides of segment 446. In some implementations, barbs 454 may be symmetrically or asymmetrically located about the axis or centerline of segment 446. Although barbs 454-1 and barbs 454-2 are illustrated as being on direct opposite sides of the centerline of the segment 446, in other implementations, barbs 454 may be axially and/or circumferentially staggered or offset relative to one another with respect to the longitudinal axis of segment 446. In yet other implementations, segment 446 may include a fewer or greater number of such barbs 454. In some implementations, suture segment 446 may be formed from the same material described above with respect to segment 34. In some implementations, segment 446 may have shape memory. For example, segment 446 may inherently have an inverted U shape in memory, wherein segment 446 resiliently returns to this shape upon being separated from carrier line 444 (upon breaking of connectors 448).

Figure 14:
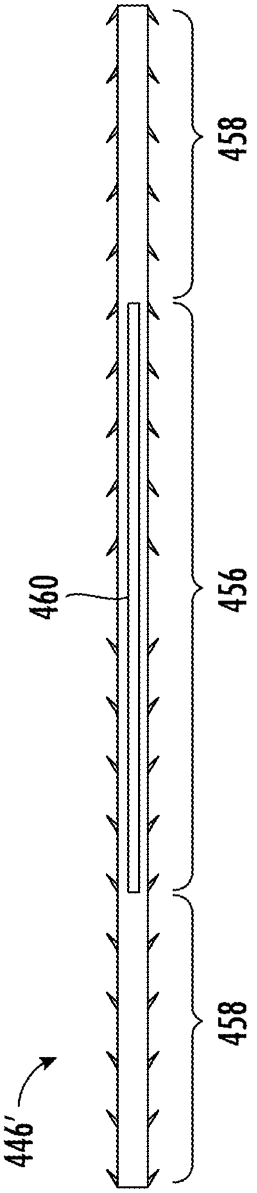
FIG. 14 is a perspective view illustrating an example suture segment.

FIG. 14 illustrates an example suture segment 446'. Segment 446' is similar to segment 446 except that segment 446' may have a differing material composition along different portions of its length or may have different material properties or characteristics along different portions of its length. Some portions may be provided with different diameters. Different portions may be provided with differently shaped or differently sized barbs 454. Different portions may be provided with different concentrations or densities of barbs. Different portions may provide with different patterns or layouts of barbs.

In the example illustrated, segment 446' has a central portion 456 and tissue penetrating end portions 458. When being inserted by staple 324, central portion 456 may be received within the interior 29 of portion 26 of staple 324 while and portions 458 are received within the interior 30 of an portions 28 of staple 324. Following insertion, portions 458 remain below the surface of the tissue while central portion 556 remains above and along the surface of the tissue that was sutured. In such implementations, portions 456 of segment 446' may be provided with a composition 460 that is elastic or resiliently stretchable. In such implementations, segment 446 may be stretched by staple 324, and stretched as a result of the segment conforming to the shape of staple 324, such as where central portion 26 of staple 324 is longer than portion 456 of segment 446'. As result, central portion 456 of segment 446' is stretched during insertion or penetration into the tissue being sutured. Upon separation from staple 324, such central portions 456 contract, drawing end portions 458 towards one another to potentially better close the formed suture.

Line feeder 412 advances supply line 414 to provide a new segment 446 for forming a suture. In the example illustrated, line feeder 412 advances supply line 414, from feed reel 408 to take-up reel 410 by rotatably driving take-up reel 410 to pull a predetermined amount of supply line 414 from feed reel 408 to position a carried suture segment 446 opposite to and below staple 324. In the example illustrated, this advancement is automatic in response to and timed with respect to the application or impelling of a preceding segment 446 into the tissue being sutured by staple drive 420. In the example illustrated, this advancement is automatically performed using and in response to force manually applied to press portions of system 320 against the tissue being sutured. In other implementations, the feeding of the line 414 or the advancement of the line 414 may be performed independent of the timing at which a suture segment is impelled into the tissue being sutured. In other implementations, the advancement of line 414 may not be automatic, but may be performed in response to a separate actuation, input or trigger by a person or controller. In some implementations, rather than relying upon or utilizing force being manually applied to press portions of system 320 against the tissue being sutured to concurrently drive staple 324 into the tissue, system 320 may utilize a separate powered actuator, wherein an actuation mechanism hydraulic, pneumatic, solenoid, motor or the like is powered by a battery or other power source.

In the example illustrated, line feeder 412 comprises the aforementioned catch 430 and ratchet teeth 440, torsion spring 464, compression spring 466, and impel trigger 468. As shown by 20, catch 430 is configured to be received between consecutive ratchet teeth 440 so as to inhibit rotation of take-up reel 410 about axis 435 (when rotatably supported by spindle or axle 428). Compression spring 466 is captured between feed reel 408 and cover 424 and exerts a force pressing feed reel 408 and 410 towards wall 426 such that catch 430 is maintained within or between ratchet teeth 440 to inhibit rotation of take-up reel 410.

Figure 15:
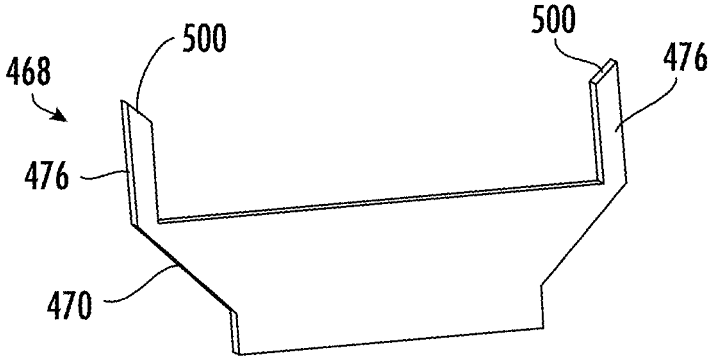
FIG. 15 is a perspective illustrating a component of the suturing system of FIG. 9.
Figure 16:
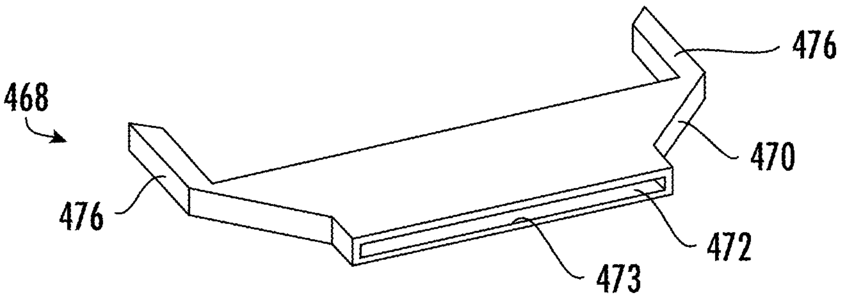
FIG. 16 is a perspective view of the component of FIG. 15.
Figure 17:
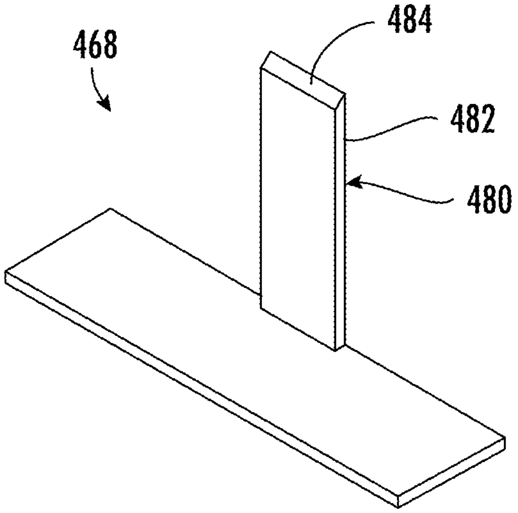
FIG. 17 is a perspective view illustrating a component of the suturing system of FIG. 9.

Impel trigger 468 functions as part of both line feeder 412 and staple drive 420. Impel trigger 468 triggers both the advancement of supply line 412 and the impelling of staple 324 into the tissue being sutured in response to the manual pressing of impel trigger 468 against the tissue being sutured, presumably across the split in the tissue being sutured. FIGS. 15-17 illustrate different portions of impel trigger 468. As shown by FIGS. 15 and 16, impel trigger 468 comprises a funnel 470 having an interior 472 which guides movement of staple 324 towards the underlying tissue being sutured. Staple 324 is moved through interior 472. The funnel 470 has a lower opening 473 through which staple 324, carrying a separated suture segment 446, passes. The funnel 470 further comprises a pair of upwardly extending actuation arms 476 for triggering or actuating remaining components of staple drive 420.

Figure 21:
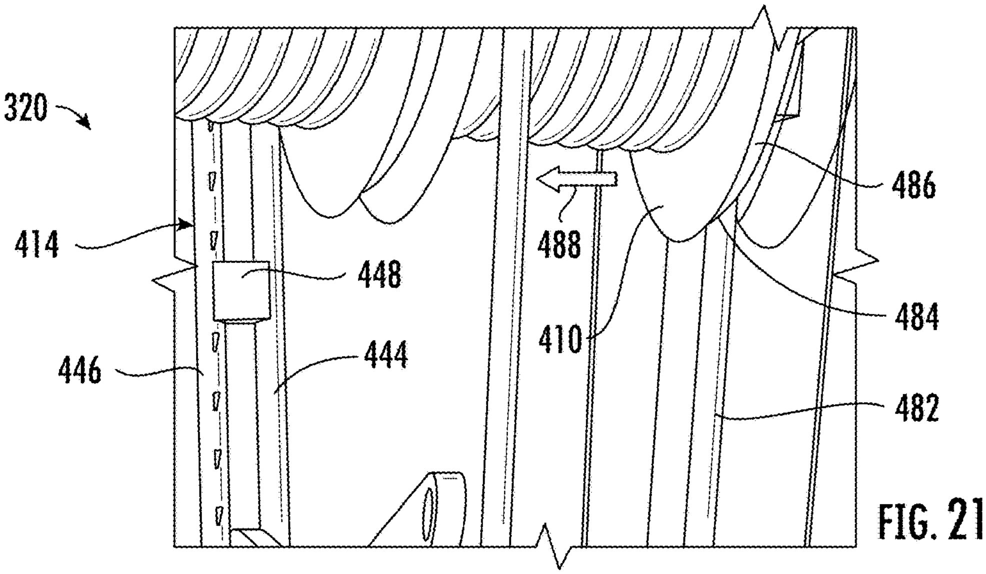
FIG. 21 is a perspective view illustrating portions of the example suturing system of FIG. 9.

As shown by FIG. 17, impel trigger 468 further comprises a reel release 480 which is joined to funnel 470 so as to move with funnel 470. Reel release 480 comprises an upwardly extending arm 482 having a ramped edge 484. As shown by FIG. 21, take-up reel 410 has a corresponding bevel surface 486. As will be described hereafter, the manual pressing of funnel 470 of impel trigger 468 against the tissue being sutured results in funnel 470 being pushed into a retracted into housing 404 and further results in arm 482 being raised such that slope or ramp surface 484 bears against bevel surface 486 to move take-up reel 410 in the direction indicated by arrow 488, against the compression provided by compression spring 466. Such movement is sufficient to withdraw catch 430 from between consecutive ratchet teeth 440. As result, torsion spring 464, having a first terminus connected to feed reel 408 and a second terminus connected to cover 424, is able to rotate reel 408 and 410 relative to cover 424 and about axis 435 provided by spindle or axle 428 until catch 430 falls into the space between the next consecutive pair of ratchet teeth 440.

In response to impel trigger 468 no longer being pressed against the tissue being sutured and the impel trigger 468 being allowed to move out of housing once again 404, ramped surface 484 is once again withdrawn from bevel surface 486 such that compression spring may once again locate catch 430 between the new pair of ratchet teeth 440. In some implementations, compression spring 466 may drive bevel surface 486 against ramp surface 44 to move impel trigger 468 from the inward retracted position that occurs during pressing of impel trigger 468 against the tissue being sutured to the extended projecting position. As will be described hereafter, in other implementations, additional springs may be utilized to return impel trigger 468 to the extended position once impel trigger 46 is no longer being pressed against or is lifted from the tissue to be sutured.

In the example illustrated, torsion spring 464 is prewound by a predetermined extent so as to incrementally rotate the take-up reel 410 by sufficient angular extent with respect axis 435 to provide a sufficient number of supply line 412 advancements so as to exhaust the number of suture segments 446 provided by feed reel 408. In other implementations, a separate mechanism may be provided for re-loading or rewinding spring 464 so as to continue to supply torque for incrementally rotating take-up real 410 for the multiple incremental advancements of supply line 412.

Each of ratchet teeth 440 has a ramp surface along which catch 430 may slide and move to a position between the next consecutive pairs of ratchet teeth 440 when released. Each of ratchet teeth 440 have stop surfaces 441 that are spaced by a distance corresponding to the length of an individual suture segment 446. Said another way, withdrawal of catch 430 from between a first pair of consecutive ratchet teeth 440 will result in rotation of take-up reel 410 by an angular extent such that supply line 414 is advanced by an extent so as to position the next successive suture segment 446 opposite to and across from staple 324.

Figure 18:
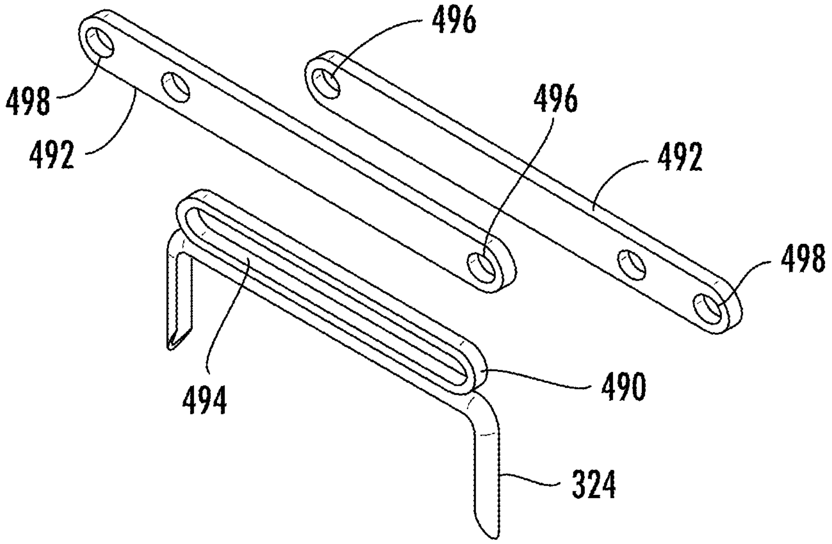
FIG. 18 is an exploded perspective view illustrating an example staple and portions of an example drive of the suturing system of FIG. 9.
Figure 19:
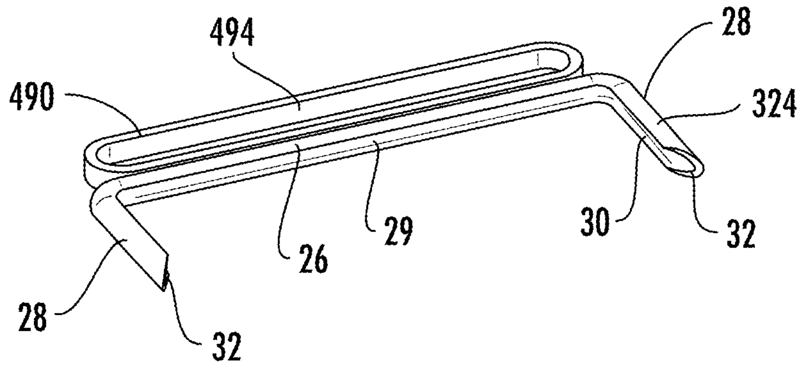
FIG. 19 is a perspective view illustrating example staple of the system of FIG. 9.
Figure 22:
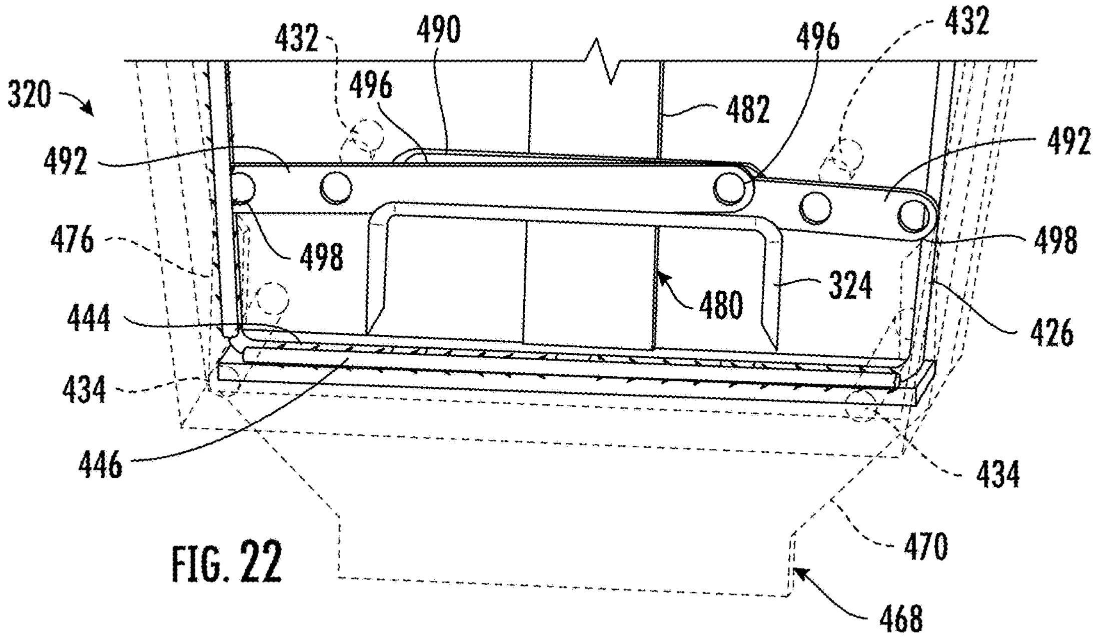
FIG. 22 is a sectional view illustrating portions of the example suturing system of FIG. 9.

Staple drive 420 is shown in FIGS. 18, 19 and 22. FIG. 22 Illustrate staple drive 420 with impel trigger 468 in the projected extending, default or resting position and with staple 324 and a retracted state generally above and opposite to an individual suture segment 446 supported by carrier line 444. Staple drive 420 generally comprises guide channel 490, drive links 492 and impel trigger 468. As shown by FIGS. 18 and 19, guide channel 490 comprises an elongate loop or other shape structure forming an interior channel or slot 494 extending across a top of staple 324. Guide channel 490 is fixed to staple 324 so as to move with staple 324.

Drive links comprise elongate rods or bars. As shown by FIG. 22, guide links 492 are pivotally supported by pivot rods 432 at a location between opposite ends. Each of drive links 492 has a first end 496 rotatably and slidably captured within slot 494 and a second end 498 engaging or operably coupled to arms 476 of funnel 470 of impel trigger 468. In the example illustrated, each of arms 476 comprises a ramp surface 500 configured to butt against a respective end 498 such that upward movement of funnel 470 during the pressing of funnel 470 against the tissue being sutured, pivots links 492 in opposite directions about pivot rods 432. In other implementations, each of arms 476 may alternatively be pivotably connected to ends 498 of drive links 492.

Figure 20:
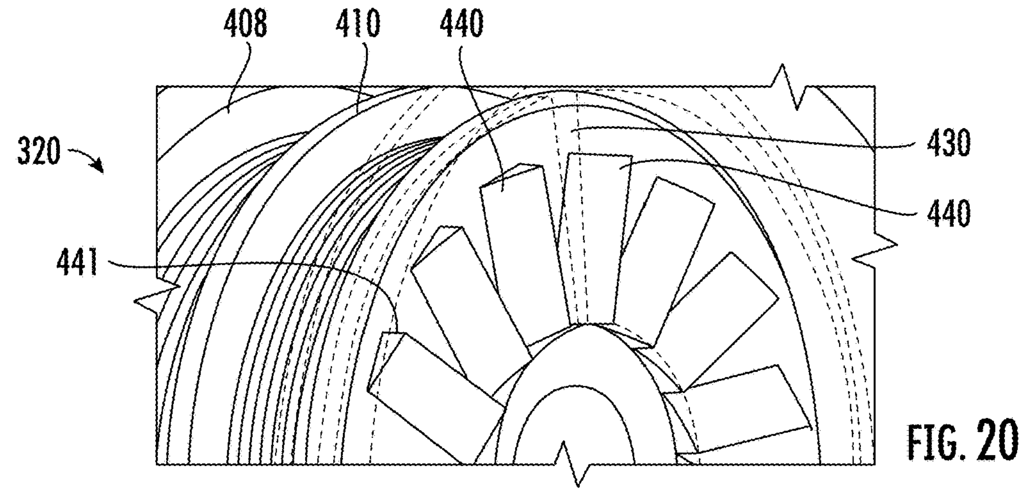
FIG. 20 is a perspective view illustrating portions of the example suturing system of FIG. 9.
Figure 23:
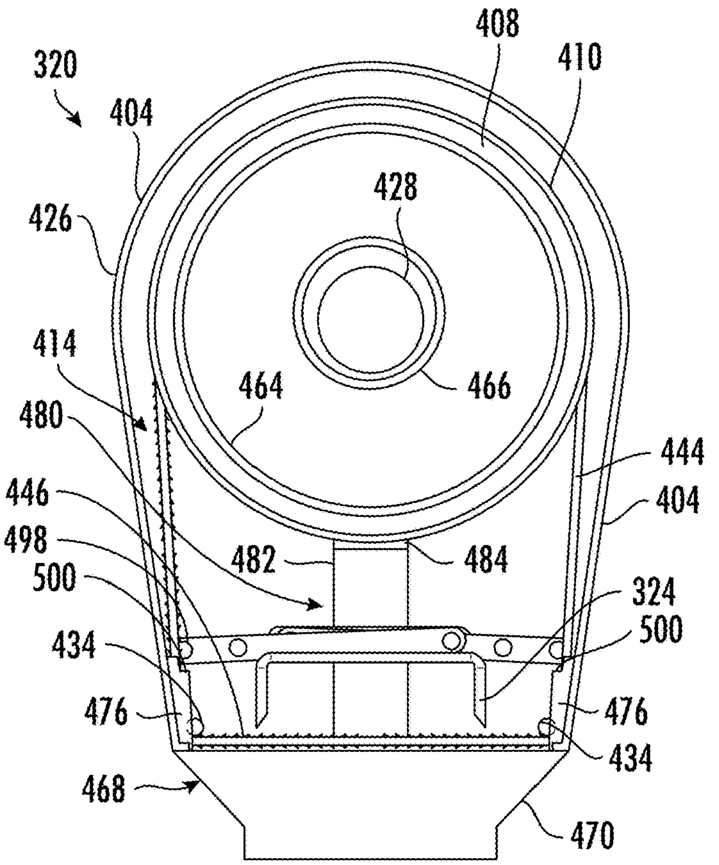
FIG. 23 is a sectional view illustrating portions of the example suturing system of FIG. 9.

FIGS. 23-26 illustrate an example application of a suture to underlying tissue 41. FIG. 23 illustrates system 320 in a ready state, prior to contact or engagement of funnel 470 of impel trigger 468 with the tissue 41 being sutured. As shown by FIG. 23, suture segments 446 is extended or spanned below and across staple 324 by guide rods 434. Funnel 470 is in the fully extended or "ready" state projecting from housing 404. Ramp surface 484 of the arm 482 of reel release 480 is out of engagement with bevel surface 486 of take-up reel 410. As result, compression spring 466 is urging ratchet teeth 440 against wall 426 such that catch 430 (shown in FIG. 10) is received between consecutive ratchet teeth 440 as shown in FIG. 20, inhibiting rotation of reels 408, 410.

Figure 24:
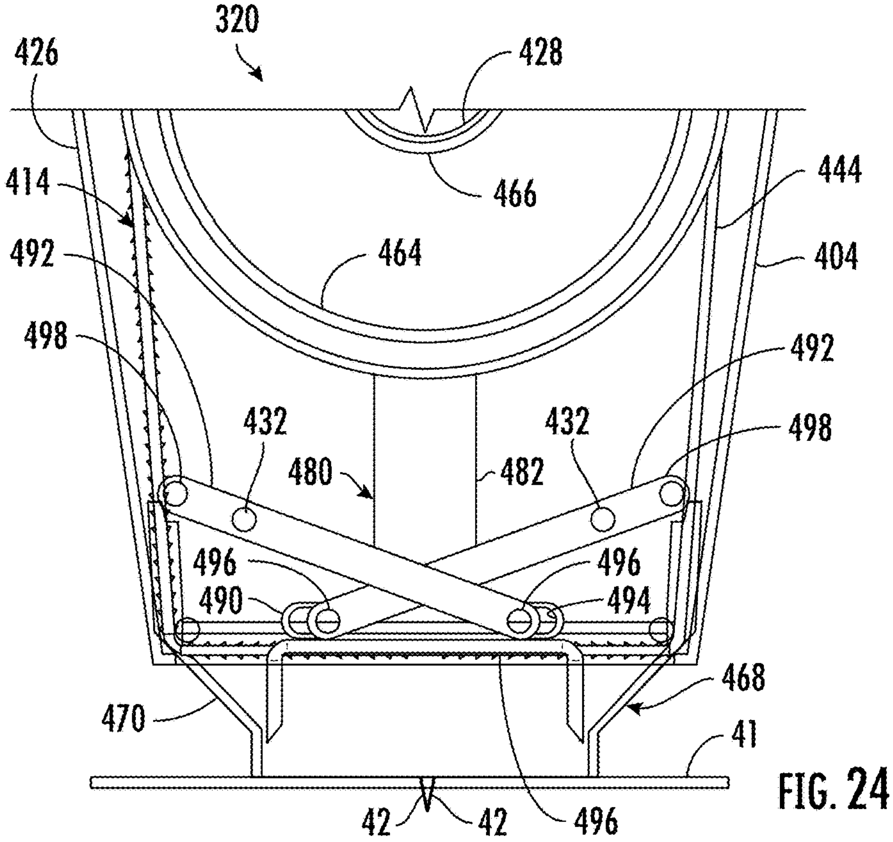
FIG. 24 is a sectional view illustrating portions of the example suturing system of FIG. 9 during driving of the example staple.
Figure 25:
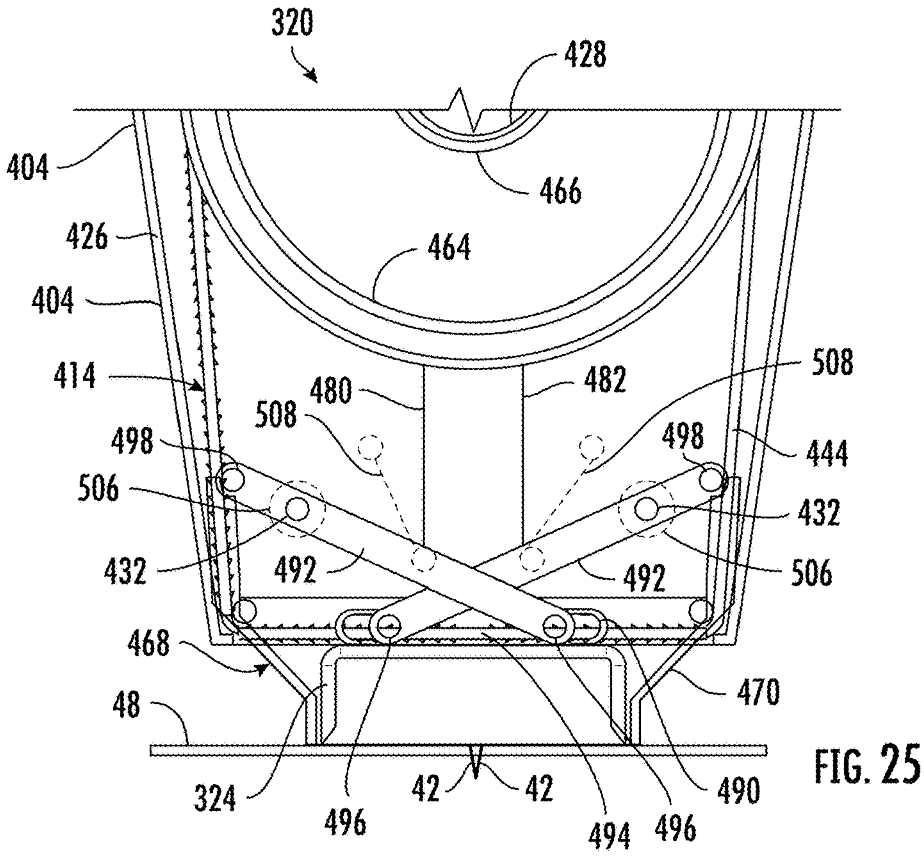
FIG. 25 is a sectional view illustrating portions of the example suturing system of FIG. 9 during driving of the example staple.
Figure 26:
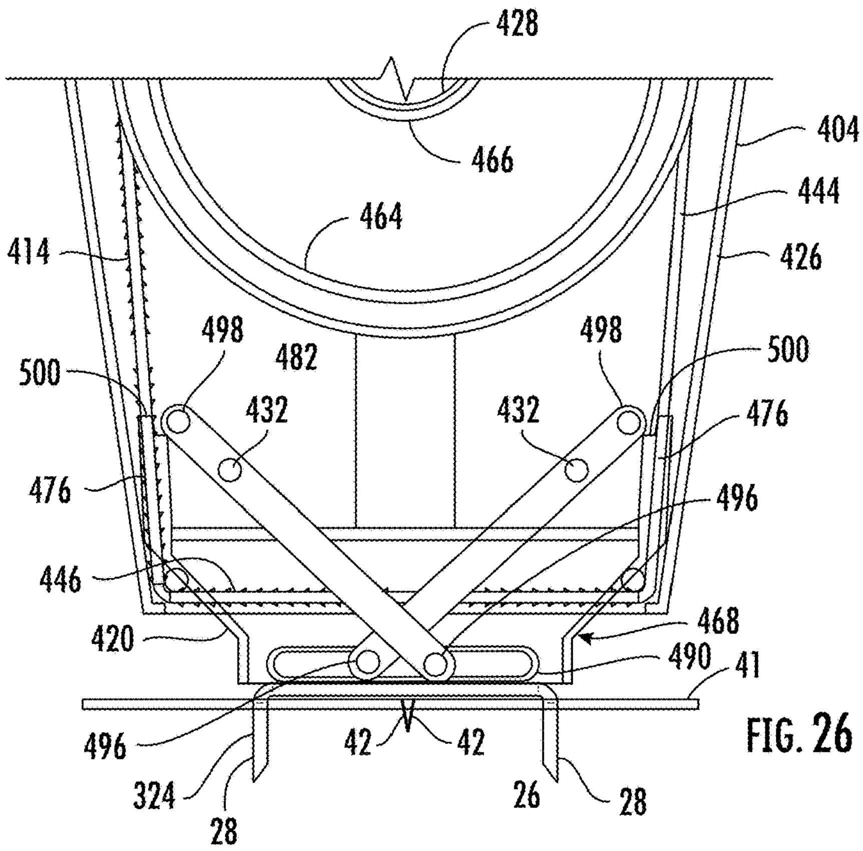
FIG. 26 is a sectional view illustrating portions of the example suturing system of FIG. 9 during implantation of a suture segment by the example staple.

FIGS. 24-26 illustrates system 320 during the pressing of impel trigger 468 against the tissue 41 being sutured, the funnel 470 being positioned across the separated edges 42 of the tissue 41 being sutured. As shown by such figures, during such downward pressing, funnel 470 and arms 476 are moved further into housing 404, wherein ramp surfaces 500 of arms 476 move up against end portions 498 of drive links 492 to pivot links 492 about the axis of pivot rods 432. This results in end portions 496 of drive links 492 pivoting and translating within the slot 494 of channel guide 490 to drive staple 324 downward, through funnel 470 as funnel 470 is being raised into housing 404. During such downward movement, staple 324 engages the underlying suture segment 446 and separates the suture segment 446 from the carrier line 444. The suture segment 446 bends into the shape of staple 324, being received within the interiors 29 and 30 of staple 324. As shown by FIG. 26, such downward movement continues until staple 324 has impelled tissue 41 and end portions 28 extend below the surface of tissue 41 with central portion 26 lying above the surface of tissue 41.

As funnel 470 is pressed against the tissue being sutured, arm 482 of reel release 480 is also carried and moved upwardly, moving ramp surface 484 into engagement with bevel surface 486 so as to push take-up reel 410 against the force of compression spring 466 and away from wall 426 by a sufficient distance so as to withdraw catch 430 from between consecutive ratchet teeth 440. As result, torsion spring 464 is allowed to rotate the take-up reel 410 such that catch 430 is moved to a location between the next consecutive pair of ratchet teeth 440 and such that supply line 414 is advanced to position the next consecutive suture segment 446 ready for the next suturing act.

Following the state shown in FIG. 26, system 320 may be lifted away from surface of tissue 41. As a result, impel trigger 46 may return to the ready state shown in FIG. 23. During such lifting, compression spring 466 may once again drive bevel surface 486 against ramp surface 484 to downwardly drive arms 482 so as to assist in moving impel trigger 46 back to the ready state shown in FIG. 23. As shown in broken lines in FIG. 25, in some implementations, the automatic return of impel trigger 46 and system 320 to the ready state shown in FIG. 23 may be further facilitated or alternatively facilitated through the use of one or more springs. For example, in some implementations, system 320 may additionally comprise torsion springs 506 (schematically shown) having a first terminus connected to housing 404 and a second terminus connected to a respective drive link 492, wherein the torsion springs 506 are configured to rotatably bias links 492 to the state shown in FIG. 23. During suturing, such springs 506 may be wound. In some implementations, system 320 may additionally or alternatively comprise tension springs 508 (schematically illustrated) having a first terminus connected housing 404 and a second terminus connected to respective drive links 492, wherein tension springs 508 resiliently bias drive. links 492 to the ready state shown in FIG. 23 and wherein such tension springs 508 are resiliently stretched during the suturing process shown in FIGS. 24-26.

Figure 27:
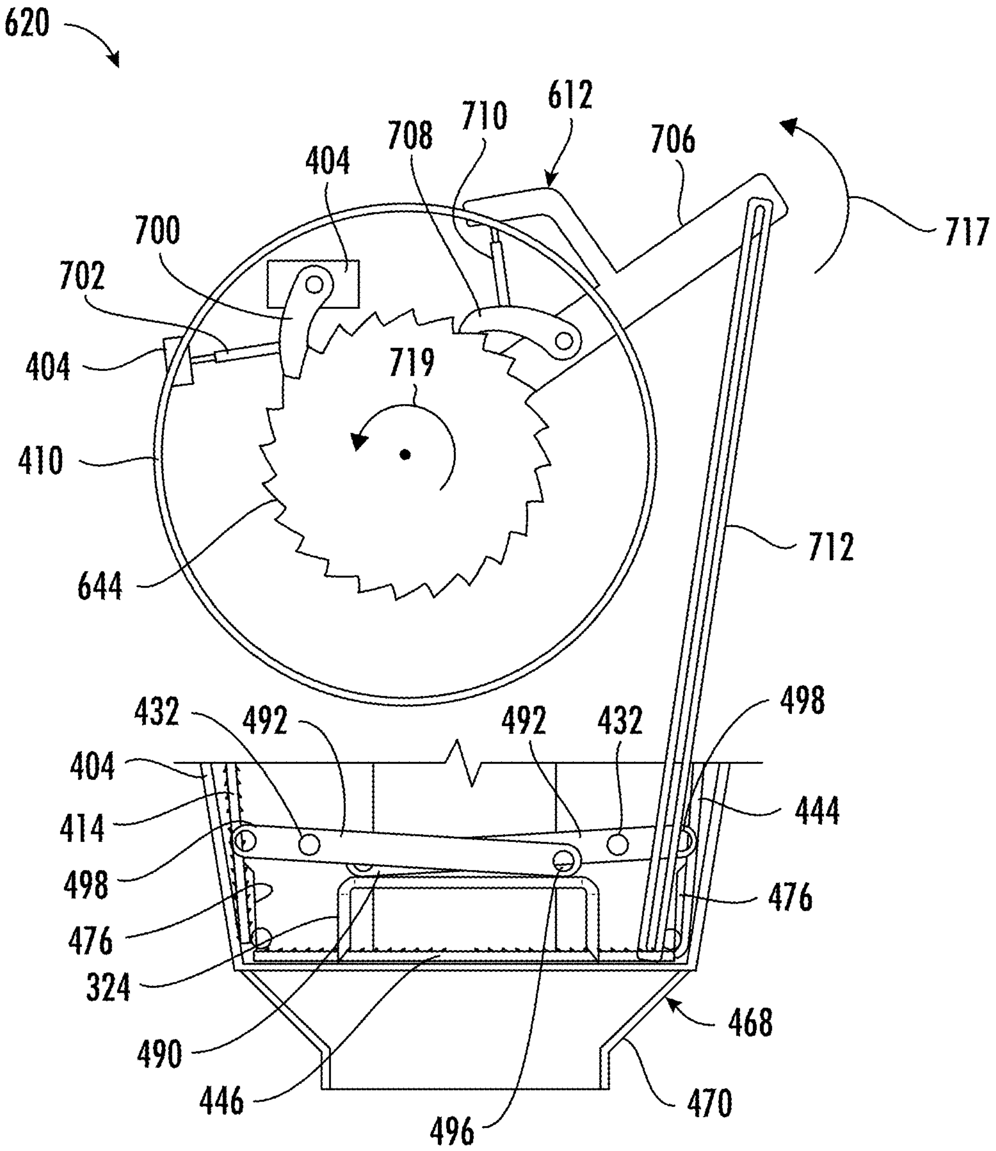
FIG. 27 is a sectional view illustrating portions of an example suturing system.

FIG. 27 is a diagram illustrating another example suturing system 620. System 620 is similar to system 320 described above except that system 620 comprises line feeder 612 in lieu of line feeder 412. Those remaining components of system 620 which correspond to components of system 320 are numbered similarly in FIG. 27 and/or are shown and described above with respect to FIGS. 8-26.

Line feeder 612 comprises ratchet teeth 644, locking pawl 700, bias 702, arm 706, driving pawl, and 708, bias 710, and feed link 712. Ratchet teeth 644 are similar to ratchet teeth 440 and are coupled to or fixed to take-up reel 410 so as to rotate in unison with take-up reel 410. Locking pawl 700 is pivotally supported by housing 404 and engages ratchet teeth 644. Locking pawl 700 is resiliently biased to an engaged state or position by bias 702 which may be a spring or other bias mechanism. The example illustrated, bias 702 is illustrated as a compression spring captured between pawl 700 and housing 404. In other implementations, bias 702 may comprise a torsion spring having terminuses secured to housing 404 and pawl 700.

Driving pawl 708 is pivotably supported by arm 706 and is an engagement with ratchet teeth 644. Driving pawl 708 is resiliently biased towards an engaged position with ratchet teeth 644 by bias 710. Bias 710 may be in the form of a compression spring captured between arm 706 and pawl 708 or a torsion spring having terminus is connected to arm 706 and pawl 708. Feed link 712 comprises a bar, rod or other structure having a first end pivotally connected to arm 706 and a second end pivotably connected to impel trigger 468. During pressing of impel trigger 46 against the tissue being sutured, force is transmitted by link 712 to arm 706 so as to pivot arm 706 in a direction generally indicated by arrow 717 so as to move driving pawl against ratchet teeth 644 to rotate ratchet teeth 644 and take-up real 410 in the direction indicated by arrow 719 so as to advance supply line 414 to position the next successive suture segment 446 in a position ready for a future operation.

Figure 28A:
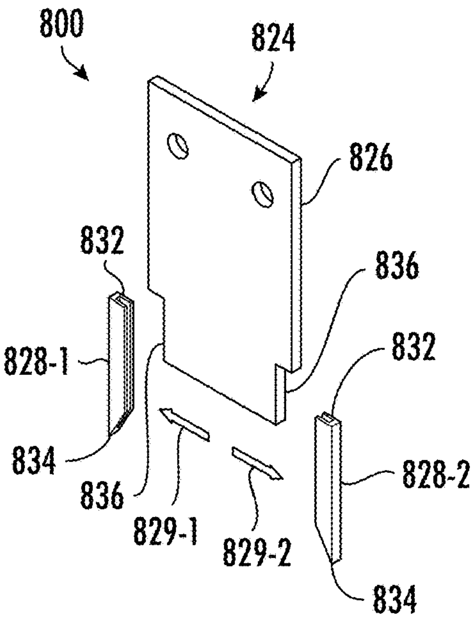
FIG. 28A is an exploded perspective view illustrating an example staple.
Figure 28B:
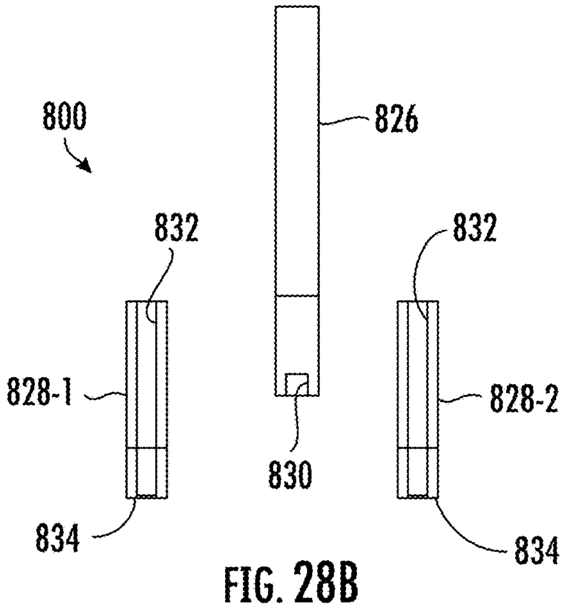
FIG. 28B is a side view of the exploded staple of FIG. 28A.

FIGS. 28A, 28B, 28C and 28D illustrate an example method 800 for forming an example staple 824. Staple 824 may be utilized in place of staple 24 or staple 324 described above. Staple 824 comprises three pieces: a body 826 and a pair of legs 828-1, 828-2. FIG. 28B provides side or edge views of body 826 and side or edge views of legs 828-1 and 828-2 taken in directions indicated by arrows 829-1 and 829-2, respectively. As shown by FIG. 28B, body 826 comprises a lower edge having an upwardly extending channel 830 that faces downwardly. Legs 828 comprise inward, mutually facing channels 832 and pointed tips 834.

In one example implementation, each of the three pieces may be cut from a thin sheet of material, such as a send sheet of metal. In one example implementation, each of channels 830 and 832 may be formed by a splitting saw. Because each channel may be milled straight through, a large splitting saw may be used as a tool radius will not affect the cut. In other implementations, the three channels may be formed or other material removal processes or may be molded.

Figure 28C:
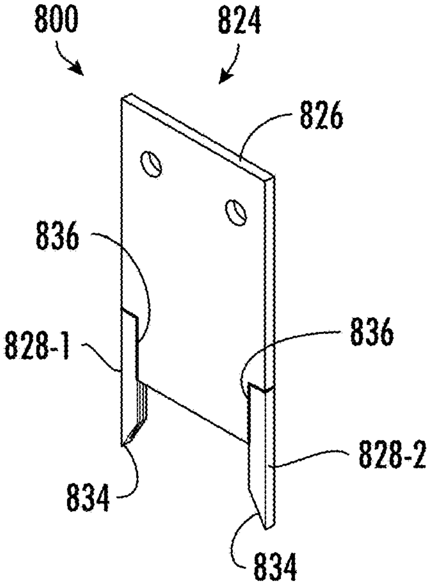
FIG. 28C is a perspective view of the assembly of the example staple of FIG. 28A.
Figure 28D:
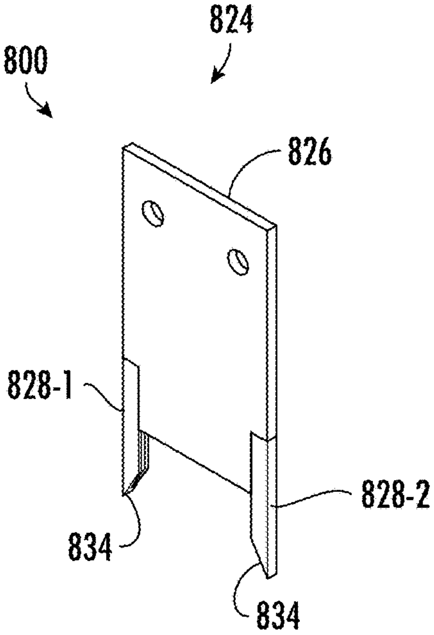
FIG. 28D perspective view of the assembled staple of FIG. 28A.

As shown by FIG. 28C, each of the three pieces are then joined. The legs 828 are secured within notches 836 located on opposite ends of channel 830 and on opposite edges of body 826. In one example implementation, the three pieces may be placed in a locating jig and joined by laser welding to form the completed staple 824 shown in FIG. 28D. When joined, the inwardly facing channels 832 and the horizontal upwardly extending channel 830 form a continuous U-shaped recess or channel for receiving a suture.

In some implementations, the legs 828 may be short as shown or may extend along or run the full vertical height (along the full length of each of the two side edges of body 826) of the body 826 for added strength. In some implementations, preformed wires having the inwardly facing channels may be utilized for legs 828. In some implementations, the preformed wires having elongate channels along their lengths may be bent and secured to body 826. In such implementations, body 826 may omit channel 830 or channel 830 may be used to receive and secure a central portion of the bent wire with the downwardly angled or bent prongs on either end of the central portion of the wire.

Method 800 facilitates the fabrication of staple 824. For example, the profile of body 826 and legs 828 may be cut by laser, punching or electrical discharge machining (EDM). Slitting saws may be utilized. Laser welding may be utilized for joining the pieces with precise welds. Although likely to leave burrs that need to be removed, laser cutting and milling may also be employed in method 800.

Method 800 and the configuration of staple 824 facilitate less complex and inexpensive manufacture of staple 824. As indicated above, in some implementations, staple 24 may be formed with minimal custom tooling aside from simple jigs. In addition, method 800 and the configuration of the staple 24 are compatible with materials such as stainless steel and titanium. The above method 800 facilitates the creation of full, deep slots or channels 830, 832 with the sharp tips 834, either sharp points or sharp corners.

Figure 29A:
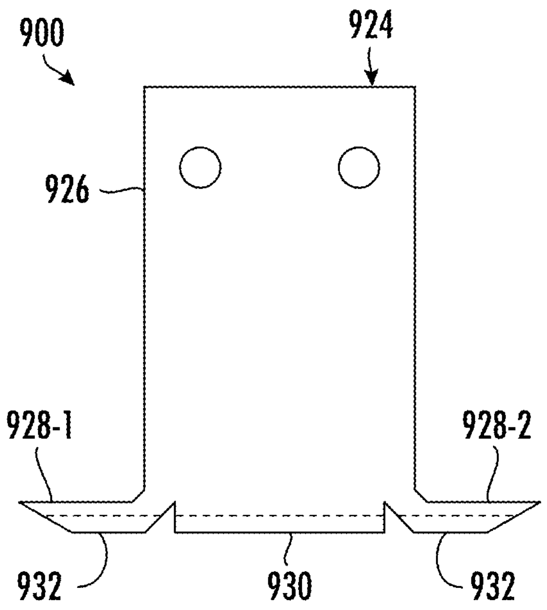
FIG. 29A is a front view of an example staple blank.
Figure 29B:
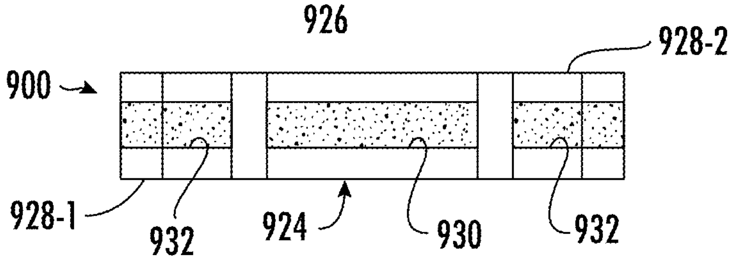
FIG. 29B is a bottom view of the example staple blank of FIG. 29A.
Figure 29C:
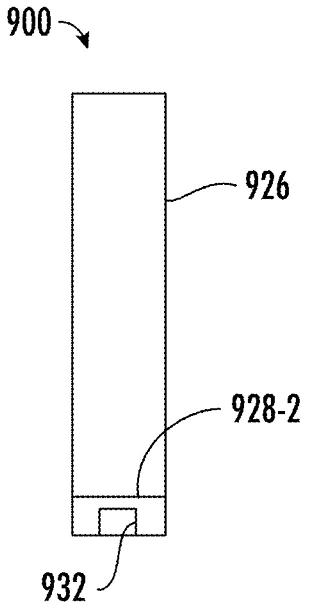
FIG. 29C is a side view of the example staple blank of FIG. 29A.
Figure 29D:
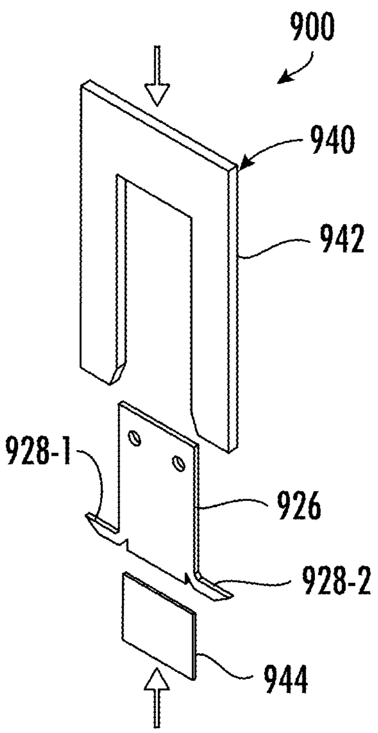
FIG. 29D is a perspective view illustrating positioning of an example die position with respect to the staple blank of FIG. 29A.

FIGS. 29A, 29B, 29C, 29D, 29E and 29F illustrate an example method 900 for forming an example staple 924 (the completed form of which is shown in FIG. 29D. As shown by FIG. 29A, the entire staple 924 is cut as an unfolded flat pattern in a sheet of material, such as a sheet of stainless steel or titanium. As further shown by FIG. 29A, the unfolded flat pattern comprises a body 96 and a pair of legs 928-1, 928-2 (collectively referred to as legs 928). While in a flat or unbent state, an upwardly extending groove or channel may be formed in the lower edge of body 926, forming channel 930 and in the bottom or lower edge of legs 928, forming channels 932. FIG. 29B is a bottom view of the unbent staple 92 while FIG. 29C is a side or edge view of the unbent staple 924. FIGS. 29B and 29C may best illustrate channel 930 in body 926 which is in communication with channels 932 in legs 928. Channels 930, 932 form a suture channel for receiving a suture.

In one example implementation, the channels 930 and 932 may be formed with a splitting saw applied to the unbent profile shown in FIG. 29A. During forming of the channel, the profile may be secured in a fixture. In some implementations, channels 932 may be bent by compression of the like to deform into the desired profile of channels 932. In other implementations, the suture slot formed by channels 930, 932 may be formed after bending of legs 928. In other implementations, the channels 930 and 932 may be formed from other processes such as other material removal processes or molding.

Figure 29E:
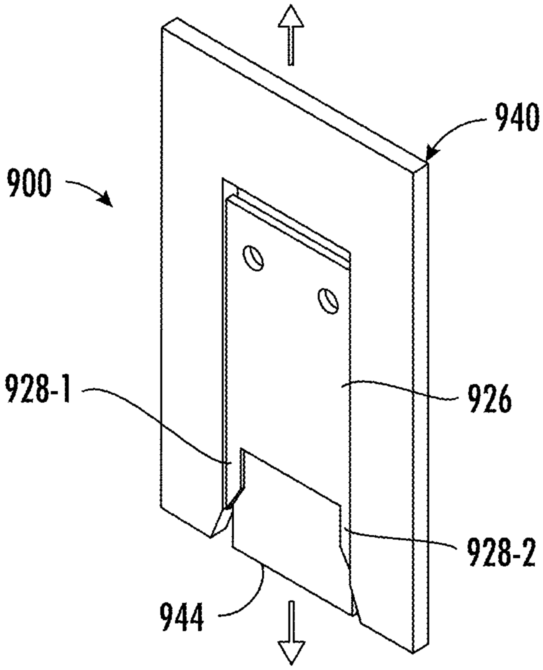
FIG. 29E is a perspective view illustrating deformation of the staple blank by the die of FIG. 29D.
Figure 29F:
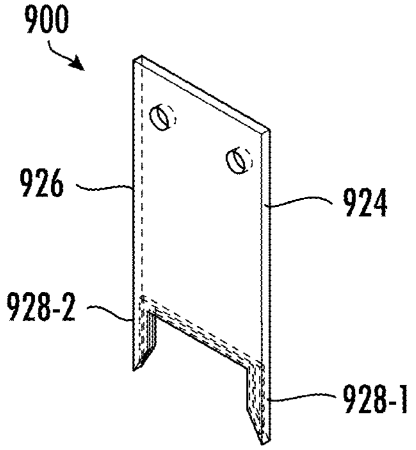
FIG. 29F is a perspective view illustrating an example staple formed by the deformation of the staple blank in FIG. 29E.

As shown by FIGS. 29D and 29E, the unbent profile shown in FIG. 29A is bent or deformed such as a legs 928 extend downwardly away from body 926, parallel to one another along the opposite side edges of body 926. In one implementation, the unbent staple 924 is placing a die for bending. In the illustrated example, the die 940 comprise a sleeve 942 which is pressed over a base 944 as shown to push the legs 928 in place. In the example illustrated, base 944 has a thickness such that base 944 is received within channels 930, 932 during the bending of legs 928. In other implementations, base 944 may have a thickness so as to not project into channels 930, 932. Thereafter, the die is separated to leave the completed staple 924 shown in FIG. 29F.

The above method 900 facilitates the fabrication of staple 924 from a variety of materials including stainless steel and titanium. Method 900 is the ability to form sharp internal corners. In some implementations, the profile shown in 29A and be cut by laser, traditional machining, punching or EDM. In some implementations, laser cutting and milling may also be utilized.

Figure 30A:
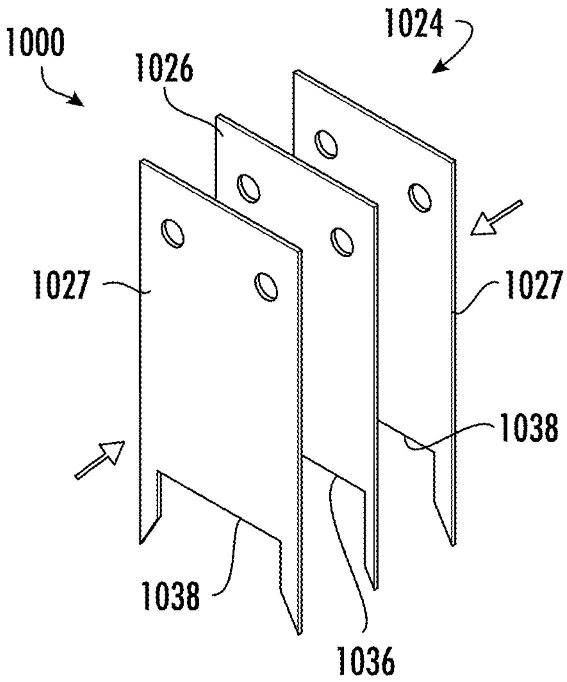
FIG. 30A is an exploded perspective view of an example staple.
Figure 30B:
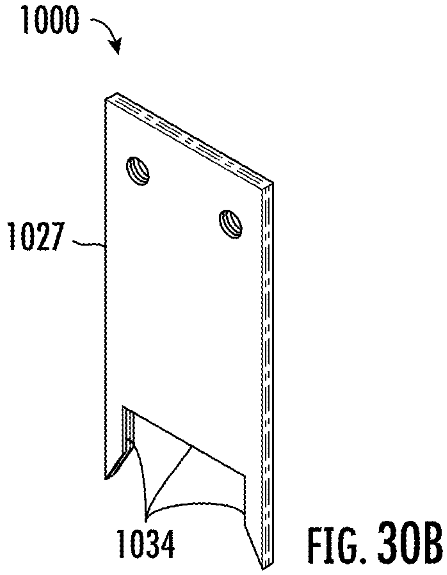
FIG. 30B is a perspective view of a portion of the example staple of FIG. 30A.
Figure 30C:
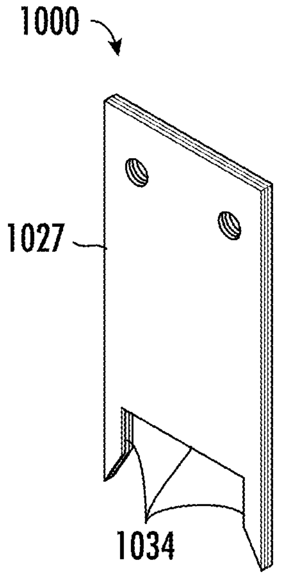
FIG. 30C is a perspective view of the example staple of FIG. 30A.
Figure 30D:
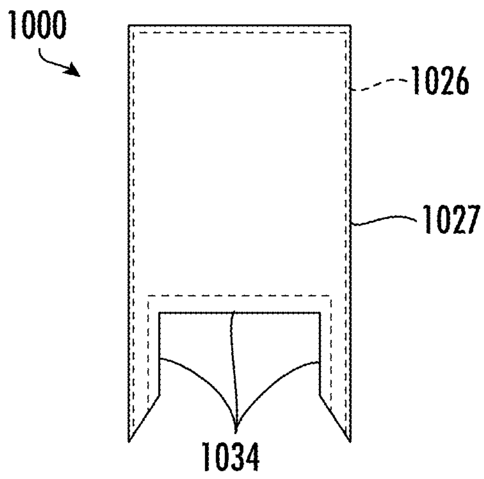
FIG. 30D is a sectional view of the example staple of FIG. 30C.

FIGS. 30A, 30B, 30C and 30D illustrate an example method 1000 for forming an example staple 1024, the completed or final form of which is shown in FIGS. 30C and 30D. As shown by FIG. 30A, staple 1024 is formed by three pieces: center plate 1026 and end plates 1027. The thickness of center plate 1026 controller defines the width of the suture slot 1034. In particular, center plate 1026 has a lower notch 1036 which is wider and deeper (higher) than the corresponding notches 1038 in end plates 1027. As result, as shown by FIG. 30D, when the three plates are joined with center plate 1026 sandwiched between and plates 1027, suture slot 1034 is formed with the edges of notch 1036 forming the ceiling or roof and interior side surfaces of slot 1034. The opposing faces of end plates 1027 extending below the top edge of notch 1036 and inwardly beyond the interior opposing edges of notch 1036 form the sidewalls of slot 1034.

In some implementations, the three plates or sheets may be cut a laser, punching or EDM. Laser cutting and milling may likewise be employed.

In some implementations, three plates or sheets may be placed in an alignment jig and laser welded together at the seams. In other implementations, sheets may be crimped together which a punch and die to mechanically join them, rather than laser welding. Method 900 offers the benefits of not requiring secondary cutting operations, but only flat sheets. Method 900 is compatible with desirable materials such as stainless steel and titanium. Method 900 may be performed with minimal specialized tooling, simple alignment and with reduced risk of tearing thin walls while milling high tolerance features.

Figure 31A:
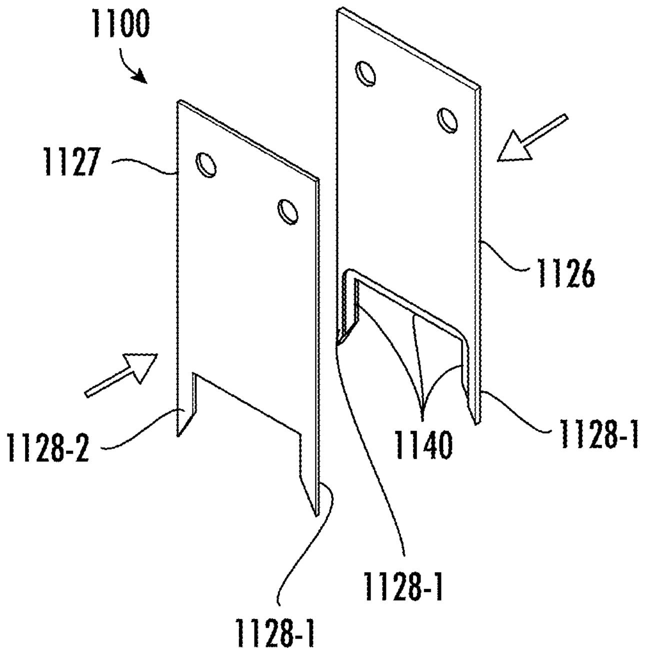
FIG. 31A is an exploded perspective view of an example staple.
Figure 31B:
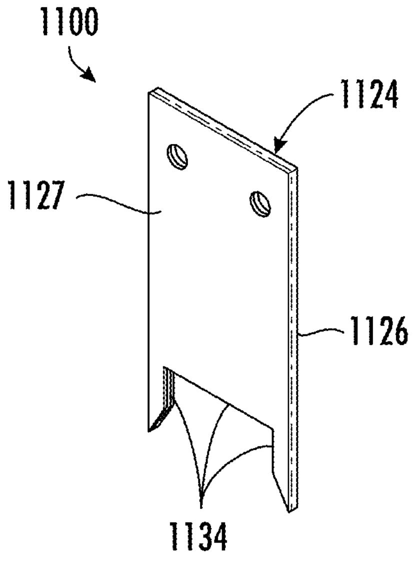
FIG. 31B is a perspective view illustrating plates of the staple of FIG. 31A positioned adjacent to one another.
Figure 31C:
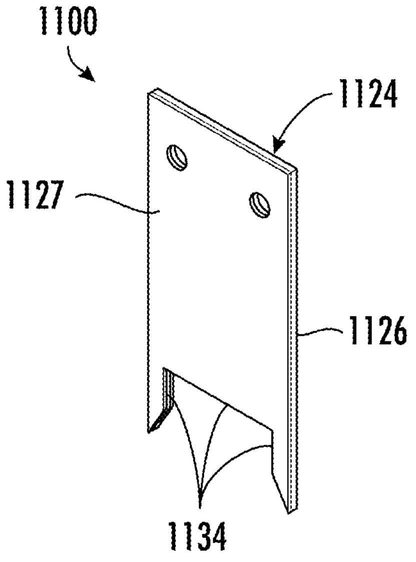
FIG. 31C is a perspective view illustrating a completed staple formed by connecting plates of FIG. 31B.

FIGS. 31A, 31B and 31C illustrate an example method 1100 forming an example staple 1124, the completed form of which is shown in FIG. 31C. As shown by FIG. 31A, staple 1124 is formed from a pair of sheets or plates 1126 and 1127 which are joined to one another so as to form a suture slot 1134. Plates 1126 and 1127 may be substantially similar to one another in that each of plates 1126, 1127 comprises a notch 1138 extending into the lower edge so as to form legs 1128. Plate 1126 additionally comprises a pocket 1140 extending into one face of plate 1126 along the edges of the notch 1138 in plate 1126. Pocket 1140 faces plate 1127. Plate 1127 serves as a "lid" for pocket 1140. When plates 1126 and 1127 are joined to one another, the surfaces of pocket 1140 form the interior edges of slot 1134 and the back interior sidewalls or side surfaces of slot 1134. The face of plate 1127 that faces slot 1134 forms the front interior sidewalls or side surfaces of slot 1134.

FIG. 31B illustrates plates 1126 and 1127 being positioned against one another. FIG. 31C illustrates the securement of the plates 1126 and 1127 to one another to form the completed staple 1124. In some implementations, plates 1126 and 1127 may be joined by laser welding. In some implementations, pocket 1140 may be milled into plate 1126. The plates may be joined in alignment jig. In some implementations, plates 1126, 1127 may be crimped together with the punch and die to mechanically join them.

Method 1100 facilitates efficient and economical production of staple 1124. Method 1100 utilizes simple alignment and minimal specialized tooling. In addition, method 1100 is compatible with many material such as stainless steel and titanium performing staple 1124. The profile of each of plates 1126, 1127 may be cut by laser, punching or EDM. Laser cutting and milling may also be utilized.

Figure 32A:
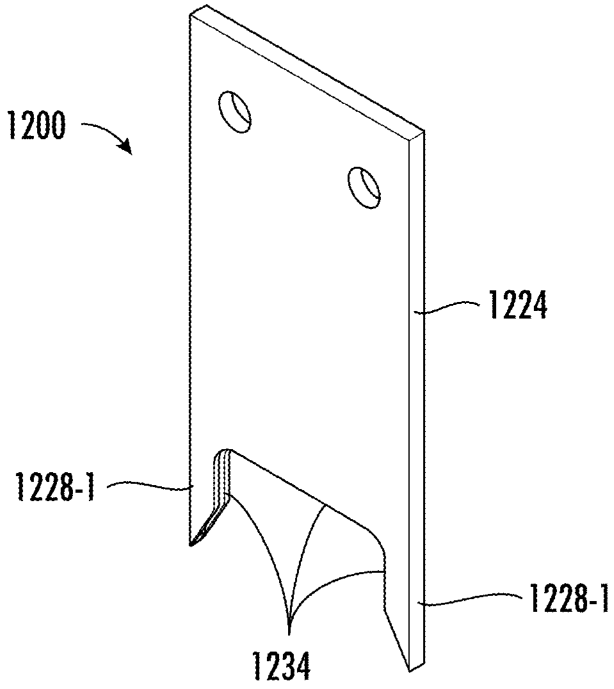
FIG. 32A is a perspective view of an example staple.
Figure 32B:
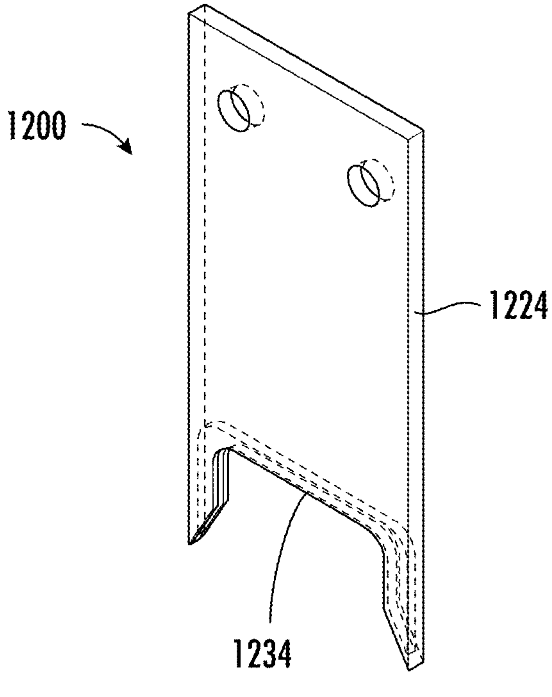
FIG. 32B is a transparent perspective view of the example staple of FIG. 32A.

FIGS. 32A and 32B illustrate an example staple 1224 formed from an example method 1200. FIG. 32B is partially transparent for purposes of illustration. With method 1200, a sheet of material is cut, such as by milling, to form the outer profile of staple 1224, including body 1226 and legs 1228. At such times, suture slot or channel 1234 is formed in the lower edge of body 1226 and the interior edges of legs 1228. In one implementation, suture slot 1240 may be formed by slitting saw of appropriate thickness and radius. As with the above methods, method 1200 is compatible with material such as stainless steel and titanium. Method 1200 may involve less precise alignment between different pieces of material. In addition, method 1200 omits welded joints. Method 1200 may yield a smooth uninterrupted suture channel 1234.

Figure 33A:
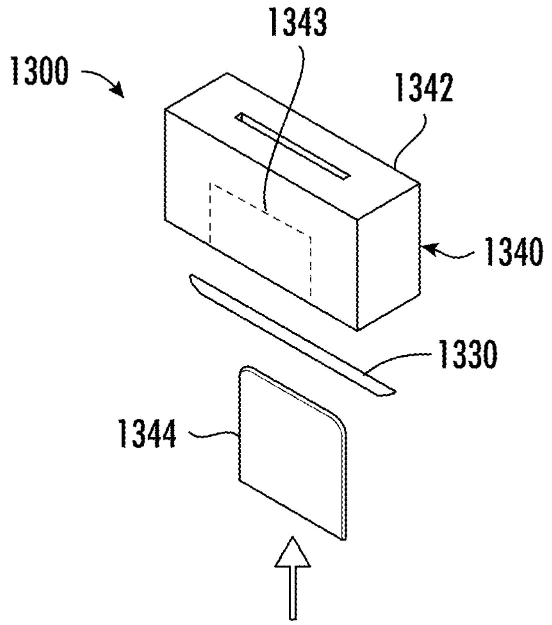
FIG. 33A is a perspective view illustrating an example method for forming an example staple.
Figure 33B:
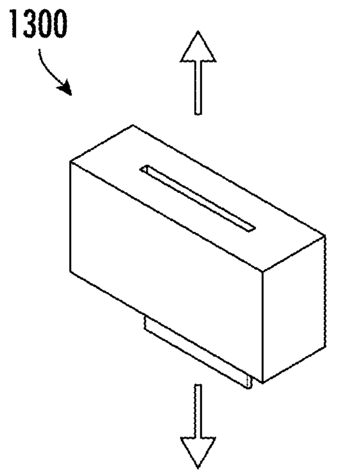

FIGS. 33A-33D illustrate an example staple 1324 (shown in FIG. 33D) performed according to an example method 1300. As shown by FIGS. 33A and 33B, a wire 1330 is bent into a staple shape by forming in a die 1340 comprising a sleeve 1342 which is pressed over a base 1344 as shown to bend the wire 1330. Wire 1330 may have a round profile which is subsequently imprinted with a channel during the forming process or may be a straight wire with a you-shaped profile. The profile may be formed by slitting saw. In some implementations, the base 1344 (also referred to as a punch) may have a thickness corresponding to the suture channel with, wherein the punch, one pressing of the wire within the cavity 1343 of the sleeve 1342 forms a staple shape with the suture slot 1334.

Figure 33C:
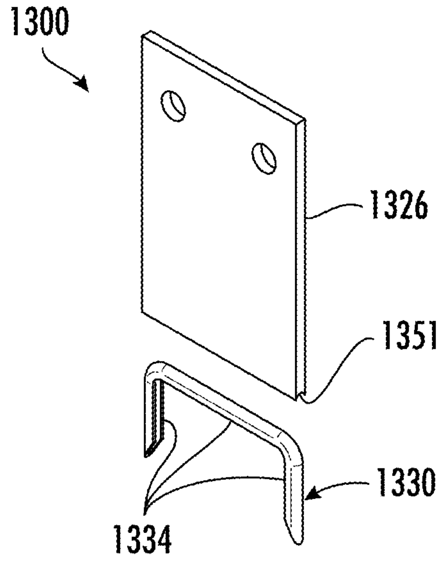
FIG. 33C is a perspective view illustrating positioning of the bent wire of FIG. 33B proximate a body.
Figure 33D:
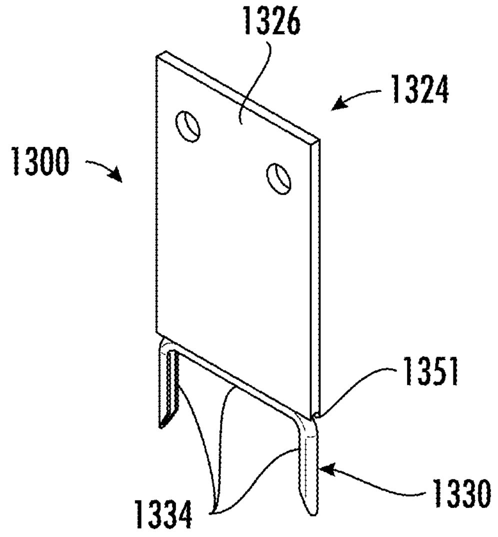
FIG. 33D is a perspective view of a completed staple formed by joining the bent wire to the body of FIG. 33C.

As shown by FIGS. 33C and 33D, the bent wire is then secured to the body 1326. In some implementations, the bent wire having the suture slot 1334 may be laser welded to body 1326. In some implementations, for added strength, body 1326 may include a downwardly facing channel or groove 1351 along its lower edge, the channel or groove receiving a central portion of the bent wire 1330. In some implementations, the channel or groove 1351 may be milled into the lower edge of body 1326. In yet other implementations, body 1326 may be formed from two pieces with a channel milled into each to accommodate outer diameter of the staple wire 1330. In some implementations, staple section may be sandwiched between the sheets, the sheets being clamped together, welded together crimped together.

Method 1300 may be compatible with stainless steel and titanium materials for the staple 1324. Method 1300 may provide a smooth, uninterrupted suture channel 1334. With method 1300, bending may be highly repeatable for production. The die 1340 may be made from a single block of metal with a channel milled in it and a sheet of metal covering the chassis two only open at the ends in which the wire is pressed. The profile of body 1326 may become by laser, traditional machining, punching or EDM. Laser cutting and milling may also be utilized.

Figure 34A:
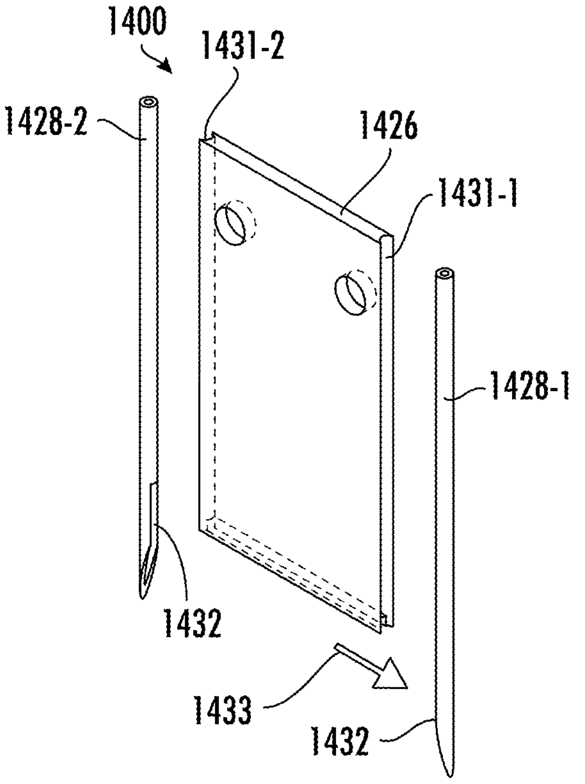
FIG. 34A is an exploded perspective view of an example staple.
Figure 34B:
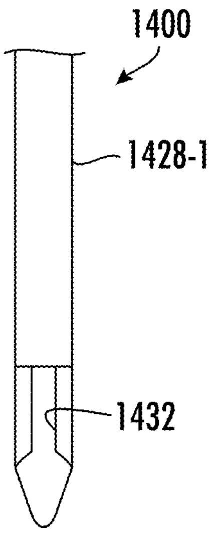
FIG. 34C is in a large perspective view of an example needle portion of the example staple of FIG. 34A.
FIG. 34D is an enlarged perspective view illustrating portions of the example exploded staple of FIG. 34A.
Figure 34C:
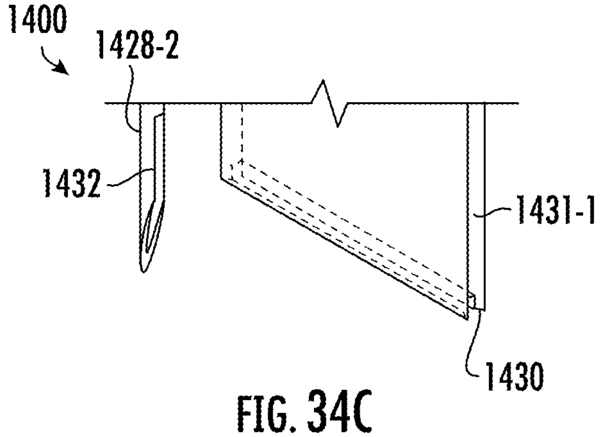

FIGS. 34A, 34B, 34C, and 34D illustrate an example staple 1424 (shown in FIG. 34D) formed by an example method 1400. As shown by FIGS. 34A, 34B and 34C, staple 1424 is formed from body 1426 and needles 1428-1, 1428-2. Body 14 having 30 and 1431. Groove 1430 extends into a lower edge of body 1426. Groove 1431 extended to opposite side edges of body 1426. Grooves 1431 are sufficiently wide and deep to at least partially receive or inset needles 1428.

Needles 1428 comprise elongate hollow pointed syringe needles having end portions that are beveled to open interior sides of the interior passages of such needles, forming channels 1432 which face one another. FIG. 30 4B is a side view of Neil 1428-1 taken in the direction indicated by arrow 1433. The openings of channels 1432 are sufficiently wide to receive the suture forming line.

Figure 34D:
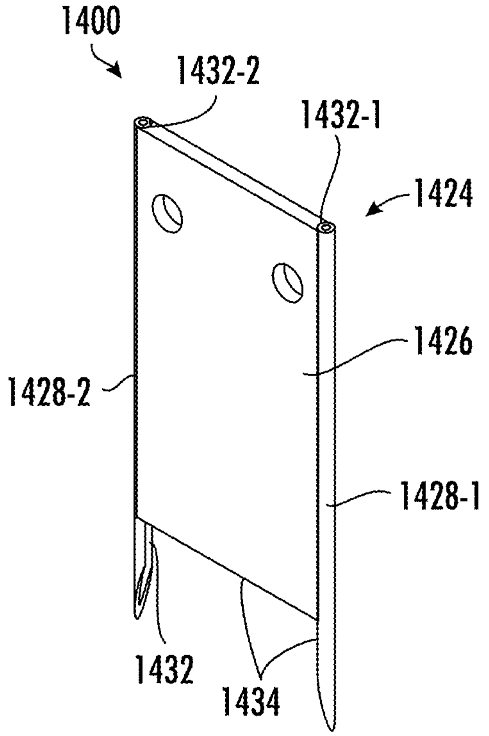

As shown by FIG. 34D, each of needles 1428-1, 1428-2 is positioned within the grooves 1431-1, 1431-2, respectively. Each of needles 1428 may be secured within such grooves by laser welding, crimps, bonds adhesives or the like. As result, a suture slot 1434 is formed by channel 1430 and the channels or grooves 1432 provided by the two opposing needles 1428.

FIGS. 35A, 35B, 35C and 35D illustrate an example staple 1524 (shown in FIGS. 35B and 35C) formed by an example method 1500. Method 1500 is similar to method 1400 except that needles 1428-1 and 1420-2 are passed through bores 1531-1 and 1531-2, respectively, wherein the lower beveled portions and exposed channels 1432 project beyond the bores 1531 to form side channel of the suture slot 1534. As shown by the exploded view of FIG. 35A, staple 1524 comprises body 1526 and syringe needles 1428-1, 1428-2 (described above). Like body 1426, body 1526 comprise a lower edge having a groove 1530. As noted above, body 1526 further includes bores 1531.

Figure 35A:
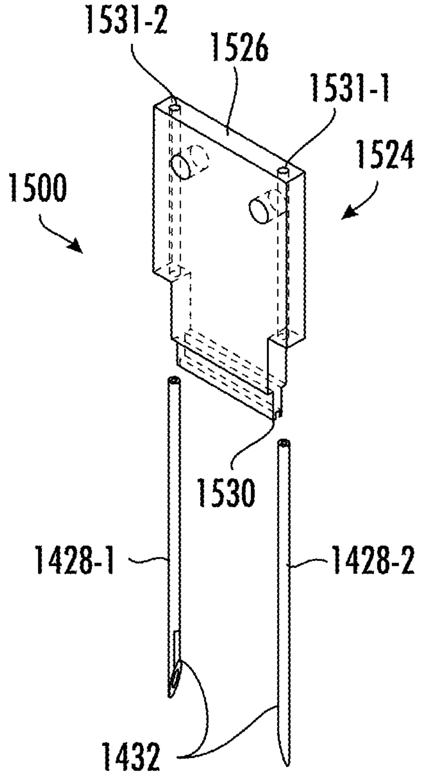
FIG. 35A is an exploded perspective view of an example staple.
Figure 35B:
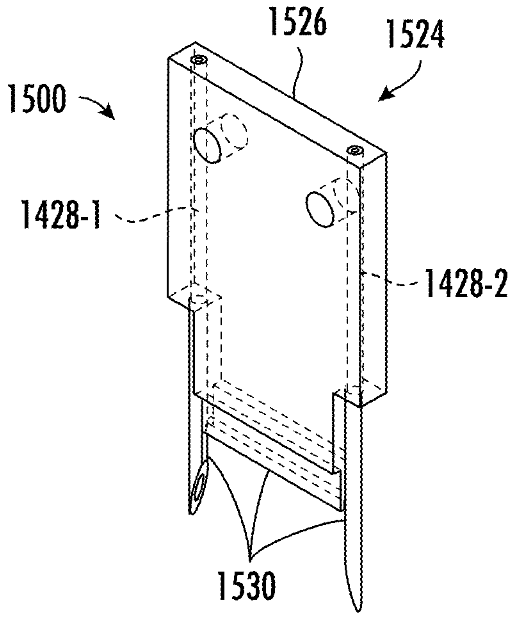
FIG. 35B is a perspective view of the example staple FIG. 35A with portions transparently illustrated.
Figure 35C:
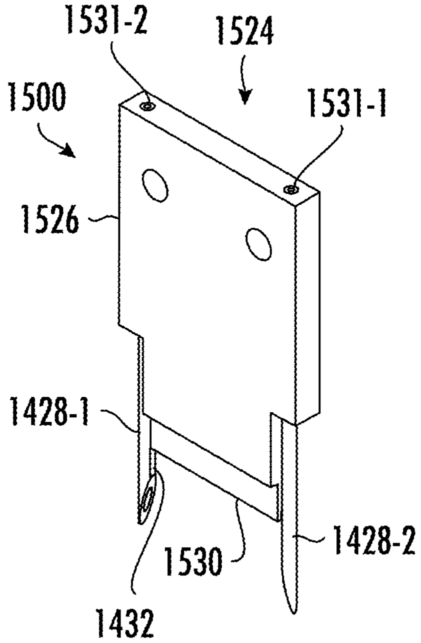
FIG. 35C is a perspective view of the staple of FIG. 35A.
Figure 35D:
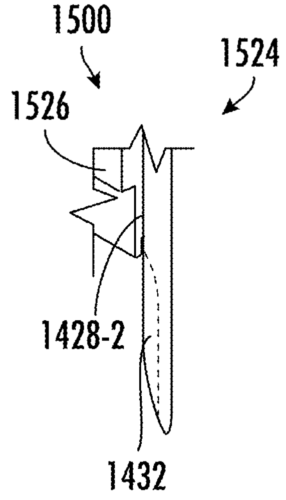
FIG. 35D is a fragmentary perspective view illustrating portions of the example staple of FIG. 35C.

Threads needles 1428 may be fixed either by laser welding compress fitting or mechanically such as with a set screw. In some implementations, adhesives may be utilized. In some implementations, the syringe needles may be removable, providing replaceable tips. As shown by FIGS. 35B, 35C and 35D, once needles 1428 have been inserted into bores 1531, lower beveled interior sides of needles 1428 and the expose channels 1430 to form the sides of suture slot 1534 while the channel or groove 1530 forms the top of suture slot 1534.

As with the above methods, methods 1400 and 1500 are both compatible with stealing titanium. Such methods provide staples that are extremely sharp with precise tips, reducing the need for precision machining operations. Fixturing may be performed with straightforward minimal special tooling. Many syringe gauges may be available. In some implementations, needle 1420 comprises a 23 gauge needle for appropriate suture receiving dimensions.

Figure 36A:
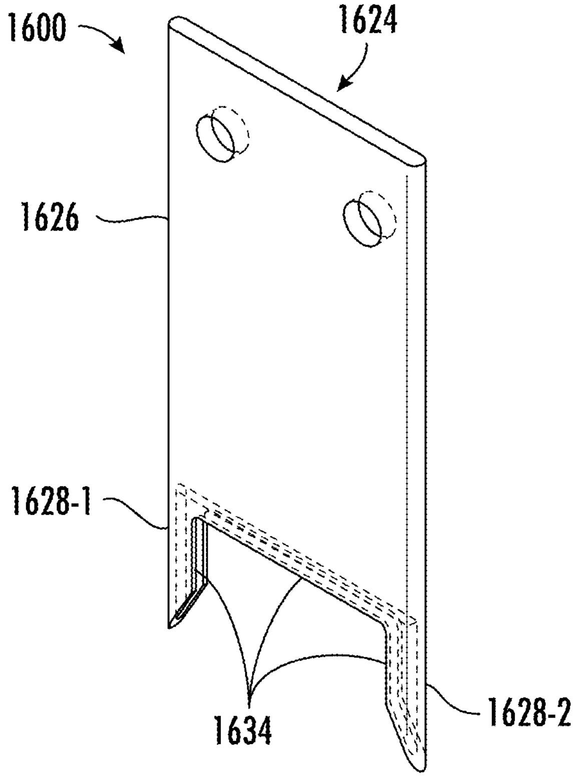
FIG. 36A is a perspective view of an example staple.
Figure 36B:
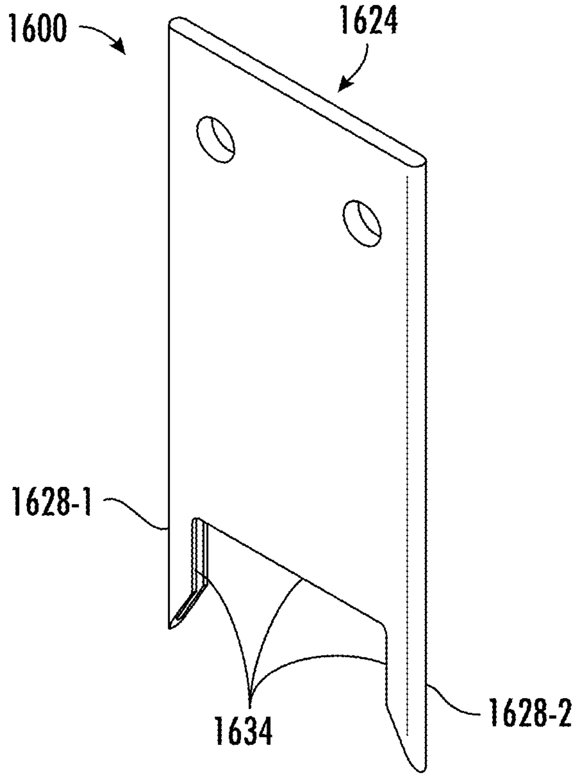
FIG. 36B is a perspective view of the example staple of FIG. 36A.

FIGS. 36A and 36B illustrate an example staple 1624 formed by an example method 1600. In the example illustrated, staple 1624 may be formed by molten metal, such as molten stainless steel, being rapidly injected into a mold and high-pressure. Once cool, staple is ejected from the mold for finishing processes. If sharp tips or desired, they may be post machined into the cast part. In the example illustrated, the staple fixing 24 is molded so as to have a body 1626 and a pair of legs 1628-11, 1628-2, the lower edge of body 1626 and the opposing mutually facing sides of legs 1628 having or forming a suture slot 1634.

The method 1600 may be utilized to diecast repeatable and scalable staple 1624. Such staple 1624 may have an uninterrupted suture channel 1634. Such staple 1624 formed by method 1600 may be produced with a low unit cost.

As indicated by broken lines, each of the individual staples shown in FIGS. 28A-36B may be additionally modified for use in the particular staple drive in which the staples are employed. For example, each of the bodies 826, 926, 1026+1027, 1126+1127 1326, 1426, 1526 and 1626 may comprise the angularly extending slot 216 (shown and described above with respect to system 120), wherein the slotted member 212 and staple 24 of system 120 may be replaced with any of the staple shown in FIGS. 28A-36B with the drive 140 being received within the slot 216 to drive the particular staple and supported suture segment.

As further shown by broken lines, in yet other implementations, each of the bodies 826, 926, 1026+1027, 1126+1127, 1326, 1426, 1526 and 1626 may comprise the slot 494 extending within or through the body or formed by a guide channel 490 in the form of an elongate loop or other shape structure mounted or fixed to a top edge of the body and forming an interior channel or slot 494 extending across a top of the staple (shown in FIG. 18). In either of such implementations, such staples may be incorporated and used as part of system 320 described above, in place of staple 324, wherein the links 492 each have an end rotatably and slidably captured within slot 494 to drive and retract the staple (as described above with respect to system 320).

FIGS. 37-40 illustrate portions of an example suturing system 1800. Suturing system 1800 comprises housing 1802, bias 1806, staple pack 1810, jaws 1814, pressure foot 1818 and staple advance 1820. Housing 1802 comprises structure supporting the remaining components of system 1800. Housing 1802 has a lower mouth 1822 through which staple pack 1810 may be moved from a retracted or withdrawn position inside housing 1802 to an extended staple inserting position in which staple pack 1810 projects beyond mouth 1822 into the underlying tissue being sutured. Housing 1802 includes channels, grooves, tabs or the like to guide relative movement of staple pack 1810, jaws 1814, pressure foot 1818 and staple advance 1820. In the example illustrated, housing 1802 supports threaded eye bolts 1827 that are threaded or otherwise secured to housing 1802 and that are secured to one end of bias 1806. In other implementations, housing 1802 may be secured to bias 1806 by other mechanisms.

Bias 1806 comprise a pair of tension springs having one end secured to eyebolt 1827 and a second end secured to staple pack 1810. Bias 1806 resiliently biases staple back 1810 and pressure foot 1818 in an upward direction away from the lower mouth 1822 and towards the withdrawn or recessed position within housing 1802. As will be described hereafter, bias 1806 further resiliently biases staple advance 1820 towards a default unactuated state. In other implementations bias 1806 may have other forms. For example, bias 1806 may comprise other forms or types of springs a biasing staple pack 1810, pressure foot 1818 and staple advance 1820. For example, in some implementations, save back 1810 and/or pressure foot 1818 may be resiliently biased in an upward direction by one or more leaf springs or compression springs a properly positioned between the bias components and housing 1802 to resiliently bias the aforementioned components in an upward direction away from mouth 1822. Rather than a single bias 1806 resiliently biasing such components, separate bias mechanism may be used to independently bias such components.

Figure 39:
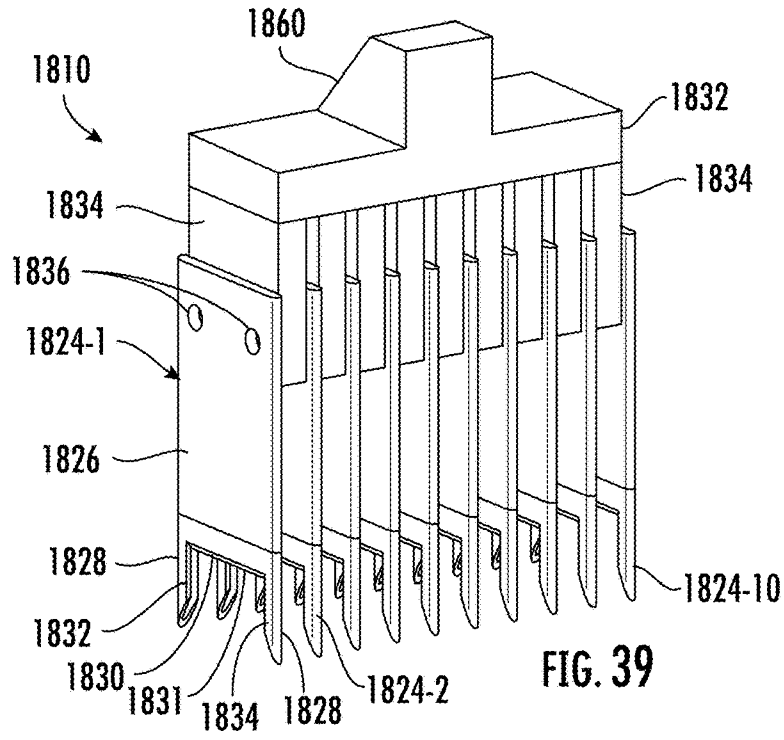
FIG. 39 is a perspective view illustrating internal components of the suturing system of FIG. 37.

Staple pack 1810 comprises a series of multiple individual staples that are moved or deployed as a unit and that contained and guide a series of flexible suture lines (described above) during penetration into the underlying tissue across a tissue separation or wound. As shown by FIG. 39, staple pack 1810 comprises staple retainer 1830 and the series of staples 1824-1 . . . 1824-10 (collectively referred to as staples 1824).

Staple holder or retainer 1830 comprises a body having a top 1832 in a series of retention arms 1834. Staples 1824 are secured along the faces of arms 1834. In the example illustrated, staples 1824 are captured between inner spaces between consecutive arms 1834 and may further be secured to the end faces of the outermost arms 1834. Such securement may be permanent in nature such as by welding, or may be releasable in nature, such as by a removable pin or pins inserted through openings 1836 in each of staples 1824 and passing through corresponding openings in each of arms 1834. In other implementations, staples 1824 may be releasably or removably secured to arms 1834 in other fashions.

Staples 1824 constitute sections of staple pack 1810, being spaced and stacked to form the length of staple pack 1810. Each of staples 1824 comprises a plate or body 1926 and prongs 1828. Body 1926 has a lower edge 1930 having an upwardly extending groove while each of prongs 1828 has an inwardly facing groove 1932 to form an inverted U-shaped suture slot 1934. The flexible suture line (also referred to as a suture segment), such as suture segment 34 or an individual segment 446, 446' (described above), is captured or received within slot 1934 (held in the inverted U-shape) until being injected into the tissue about the wound. In some implementations, the flexible suture lines are pre-inserted into the suture slot 1934 of each of staples 1824 prior to securement to arms 1834. In yet other implementations, the flexible suture lines are inserted into suture slots 1934 after such staples 1824 are secured to arms 1834. The flexible suture lines may have constructions similar to the above described suture lines.

Staples 1824 may each be formed and have a construction described above with respect to any of staples 24 or 800-1600. In yet other implementations, staples 1824 may have other configurations. In some implementations staples 1824 may alternatively be integrally formed with one another as part of staple pack 1810. Although staple pack 1810 is illustrated as comprising 10 staples 1824, in other implementations, staple pack 1810 may include a single staple, a plurality of staples less than 10 staples or a plurality of staples greater than 10 staples.

Jaws 1814 and pressure foot 1818 cooperate to pinch and/or hold those portions of tissue on opposite sides of the tissue break or wound together as staple pack 1810 is lowered such that the staples 1824 penetrate the tissue on opposite sides of the wound and release the carried flexible suture lines into the tissue across the wound or tissue break, creating the suture. Jaws 1814 comprise a pair of tissue grippers 1840-1, 1840-2 (collectively referred to as grippers 1840) that are each pivotably connected to housing 1802 for pivoting about axes 1843 between an open state shown in FIG. 40A in a closed shown in FIG. 40B. Each of grippers comprises a row of teeth 1844 to assist in gripping or engaging the underlying tissue.

Pressure foot 1818 comprises a mechanism configured to actuate grippers 1840 between the open and closed states. In the example illustrated, pressure foot 1818 comprises a member slidably reported by housing 1802 for vertical movement relative to housing 1802 between grippers 1840. As shown by FIG. 40B, in one example implementation, pressure foot 1818 may comprise a bar or tongue 1848 that slides within a vertical groove 1850 formed in housing 1802. As further shown by FIGS. 40A and 40B, pressure foot 1818 is sized and shaped to physically contact and ride against grippers 1840 above axes 1843 such that upward movement of pressure foot 1818 relative to axes 1843 pivots grippers 1840 about axes 1843 from the open state shown in FIG. 40A to the closed state shown in FIG. 40B. In some implementations, housing 1802 may slidably support a second pressure foot 1818 proximate to an opposite end of grippers 1840, wherein the two pressure foot interact with opposite end portions of grippers 1840 to pivot such grippers 1840 between the open state and the closed state.

Figure 40A:
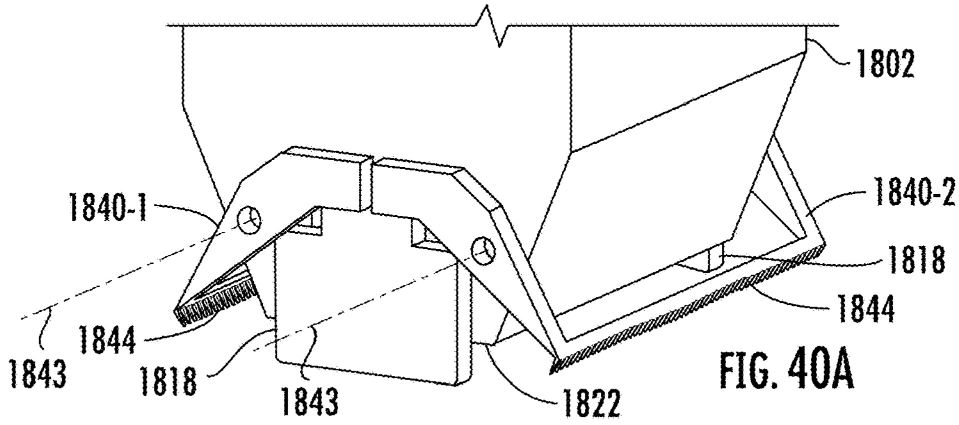
FIG. 40A is a perspective view of the suturing system of FIG. 37 with example jaws and an open state.
Figure 40B:
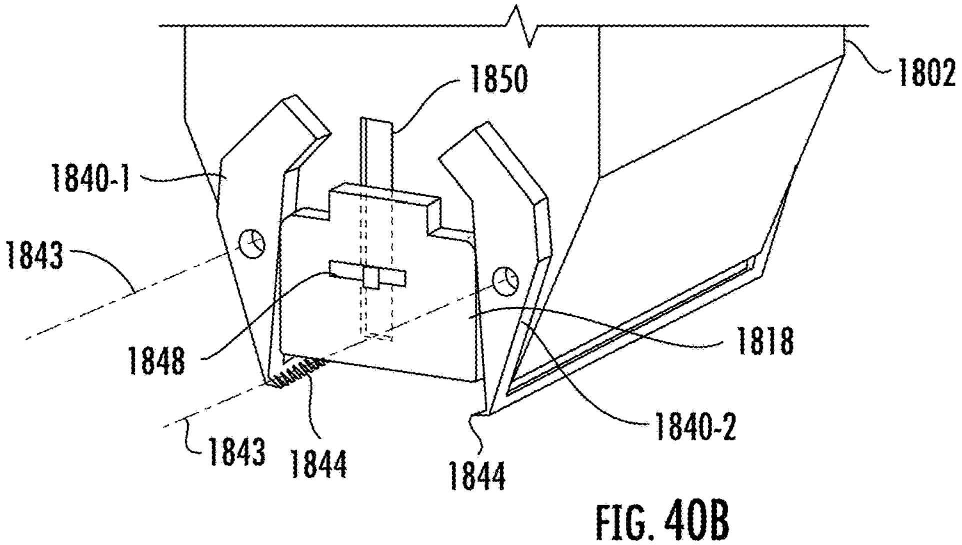
FIG. 40B is a perspective view of the suturing system of FIG. 37 with the example jaws in a closed state.

In some implementations, pressure foot 1818 (or both of pressure feet 1818) may be resiliently biased towards the lowered position shown in FIG. 40A. For example, in some implementations, pressure foot 1818 (or pressure feet 1818) may be resiliently biased by a tension spring having a first and connected to housing 1802 and a second end connected to pressure foot 1818. In some implementations, grippers 1840 may be resiliently biased towards the illustrated open state shown in FIG. 40A, wherein movement of pressure 1818 works against such bias to close grippers 1840. For example, in some implementations, grippers 1840 may be resiliently biased towards the open state by torsion springs having a first end secured to an associated one of grippers 1840 and a second end secured to housing 1802. In yet other implementations, gravity may be utilized to move pressure foot 1818 to the default lowered state shown in FIG. 40A.

In the lowered state, pressure foot 1818 extends or projects below mouth 1822. When housing 1802 is being lowered or move towards the underlying tissue, pressure foot 1818 contacts the underlying tissue first, prior to mouth 1822 being brought into contact with the underlying tissue or wound. As result, in response to the mouth 1822 being lowered into contact with and across the underlying wound, the closing of grippers 1842 is at or near completion, gripping opposite sides of a tissue break and potentially pinching opposite sides of the tissue break towards one another for subsequent suturing.

Figure 38:
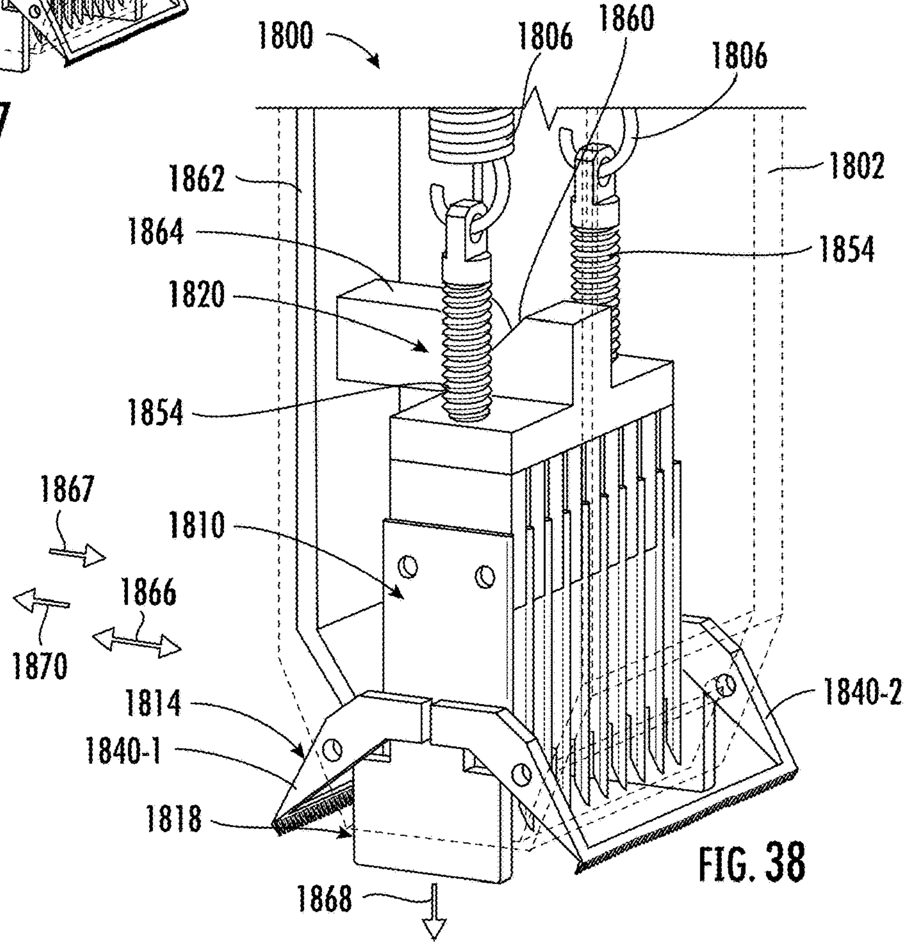
FIG. 38 is a partially transparent perspective view of portions of the suturing system of FIG. 37.

As shown by FIG. 38, staple pack 1810 is coupled to bias 1806 such that they pack 1810 is really biased towards a withdrawn or retracted position within housing 1802, above mouth 1822. In the example illustrated, system 1800 comprise a pair of eyebolts 1854 threat are screwed into top 1832 of staple pack 1810, wherein the lower end of the tension springs serving as bias 1806 are connected to such bolts. As described above, in other implementations, by bias 1806 may have other forms, wherein the connection of staple pack 1810 two such a bias may have different configurations. In the example illustrated, staple pack 1810 is releasably connected to bias 1806 to facilitate staple pack 1810 from housing 1802 for repair, replacement or refilling of staple pack 1810.

Figure 37:
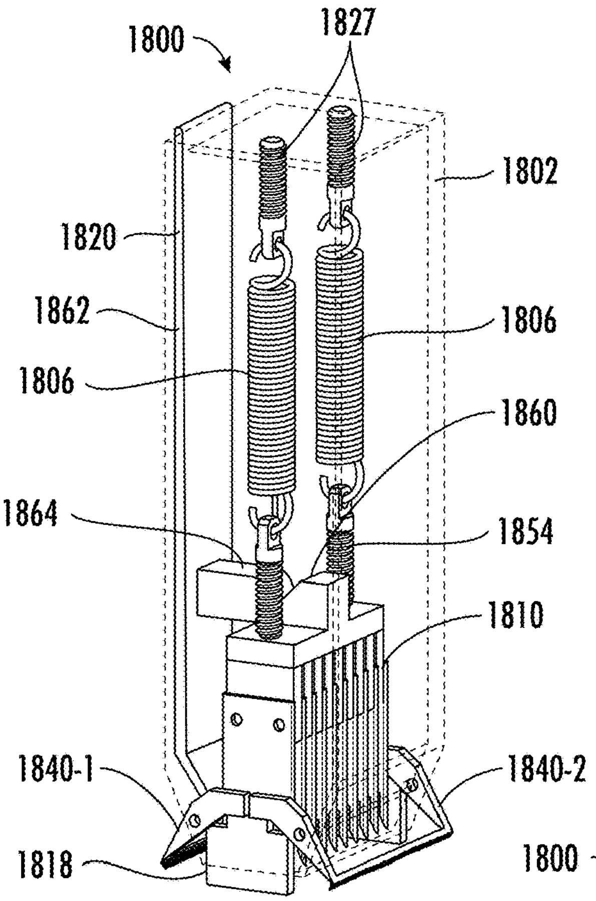
FIG. 37 is a partially transparent perspective view of portions of an example suturing system.

Staple advance 1820 comprise a mechanism configured to raise and lower staple pack 1810 relative to housing 1802, between a retracted or withdrawn position within housing 1802 and an extended tissue engaging position beyond mouth 1822. In the example illustrated, staple advance 1820 applies force against bias 1806 to lower staple vacating 10 against bias 1806 (stretching the tension springs serving as bias, wherein release of the force applied by that will advance 1820 permits bias 1806 to automatically return staple pack 1810 to the default raised, withdrawn a retracted position within housing 1802. 1806). As shown by FIGS. 37 and 38, staple advance 1820 comprises ramp 1860, push bar 1862 and drive member 1864.

Ramp 1860 comprises an upwardly facing ramp coupled to staple pack 1810. As shown by FIG. 39, ramp 18 may be integrally formed as part of top 1832. Ramp 1860 faces drive member 1864. Drive member 1864 is movably supported by housing 1802 for inward and outward movement relative to housing 1802 as indicated by arrows 1866. Drive member 1864 is movably supported along an exterior of housing 1802 for being manually pushed or depressed inwardly. In some implementations, drive member 1864 may comprise posts that are slidably movable along a channel provided in housing 1802 to guide the sliding inward and outward movement of drive member 1864.

Push bar 1862 carries drive member 1864. Drive member 1864 extends from push bar 1862 and faces ramp 1860. Drive member 1864 is configured to bear against and exert force against ramp 1860 as push bar 1862 is depressed or moved inwardly (in the direction indicated by arrow 1867) such that ramp 1860 and staple pack 1810 are driven in a downward direction (indicated by arrow 1868 against bias 1806 towards the tissue engaging extended state. Conversely, manual release of push bar 1862 (the cessation of inward force being manually applied to push bar 1862) results in bias 1806 raising staple pack 1810. During such raising, ramp 1860 bears against drive 1864 to push and move push bar 1862 outwardly in the direction indicated by arrow 1870 (the default state). In the example illustrated, drive member 1864 may itself have a ramp surface facing and bearing against ramp 1860. In other implementations, drive member 1864 may comprise a rod or bar having a tip that bears against and rides along ramp 1860.

Figures 41A, 41B, 41C, 41D, 41E, 41F:
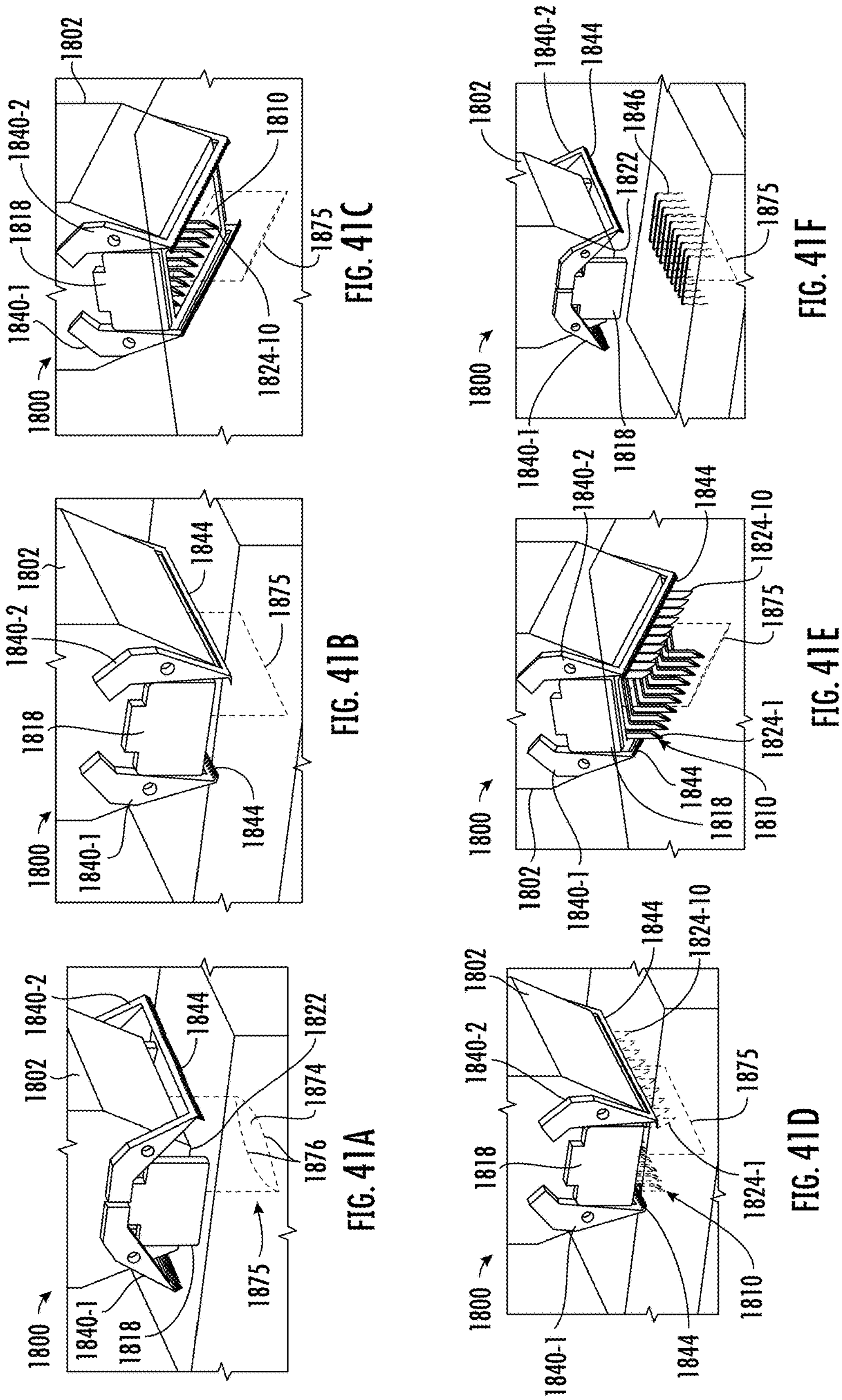
FIGS. 41A, 41B, 41C, 41D, 41E and 41F are perspective views of the system of FIG. 37 illustrating implantation of an example suture across a tissue break.

FIGS. 41A, 41B, 41C, 41D, 41E and 41F illustrate an example operation of system 1800. FIG. 41A illustrates system 1800 in an initial fund actuate state positioned against, over and across a wound 1875 in the form of a tissue break 1874, wherein opposite sides 1876 of the tissue break may be spaced from one another by a gap 1877. In FIG. 41A, pressure foot 1818 is in the lowered position, grippers 1840 are in their opened states, and pack 1810 is in the raised fund deployed state, being held by bias 1806 above and within mouth 1822 and within housing 1802.

FIGS. 41B and 41C illustrate the depression or pushing of housing 1802 in the direction indicated by arrow 1880 towards the wound 1875, without any depression of push bar 1862. Prior to mouth 1822 being brought into contact with the underlying tissue, pressure foot 1818 engage the underlying tissue. Following such initial engagement of the underlying tissue by pressure foot 1818, further lowering of system 1800 and housing 1802 results in pressure foot 1818 being slid or driven upwardly relative to housing 1802 and relative to mouth 1822 to pivot grippers 1840 from the open state shown in FIGS. 37, 38 and 42 the closed tissue gripping and pinching state shown in FIGS. 40B, 41B and 41C. As shown by FIGS. 41B and 41C, this results in opposite sides 1876 of the tissue break 1874 being drawn or pinched together to reduce the size of gap 1877 or too close gap 1877 (shown in FIG. 41A).

FIGS. 41D, 41E and 41F illustrate system 1800 applying the multiple individual spaced flexible suture lines carried by suture pack 1810 to the underlying tissue or wound 1875, across the tissue break. To "fire" the staple pack 1410, push bar 1862 is manually depressed inward (in the direction indicated by arrow 1867 in FIG. 38) against bias 1806. This results in push member 1864 driving ramp 1860 to drive staple pack 1810 downwards, through mouth 1822, past the teeth 1844 grippers 1840 and into the underlying tissue on opposite sides of the tissue break. This is performed while housing 1802 is still being depressed against the wound such that grippers 1840 of jaws 1814 are pinching opposite sides of the tissue break towards one another. In other words, the driving of the set of staples into the underlying tissue is performed while wound approximation is maintained. At such times, all of the prongs 1828 of the individual staples 1824 are penetrating the underlying tissue while carrying their respective flexible suture lines/segments.

FIG. 41F illustrates manual release of staple advance 1820 which permits bias 1806 to retract staple pack 1810 into housing 1802. During such retraction, the series of flexible suture lines or segments 1846 are left in the underlying tissue, extending across the tissue break or wound, maintaining or assisting in holding the opposite sides 76 against one another or in close approximation to one another. As described above, in some implementations, the segments 1846 may be provided with one or more barbs which further assist in gripping the underlying tissue to maintain the arms of the line/segments 1846 in place.

FIG. 41F further illustrates withdrawal of housing 802 from the underlying tissue, lifting of housing 802 in the upward direction. As a result, grippers 1840 of jaws 1814 pivot to their open state as shown. As indicated above, such pivoting may be driven by springs between grippers 1840 and housing 1802 or by compression or tension springs biasing pressure foot 1818 downwardly, outwardly beyond mouth 1822 which permits grippers 1842 to widen.

Once the flexible line/segments 1846 have been discharged from staple pack 1810 as shown in FIG. 41F, the individual staples 1824 may be reloaded with new segments 1846 while secured as part of system 1800, the exhausted staple pack 1810 may be removed and reloaded with new segments 1846, or the staple pack may be disconnected from bias 1806, remove from housing 1802 and replaced with a new or different staple pack 1810 already loaded with suture line/segments 1846. System 1800 is then ready for a subsequent suturing task with respect to another length or portion of the wound 1875 or a different wound 1875.

Although the claims of the present dis is similar to pressure foot closure are generally directed to suturing systems, methods and staples, the present disclosure is additionally directed to the features set forth in the following definitions.

1. A suturing system comprising:
a suturing device comprising:
a staple comprising a center portion and end portions extending from the center portion, the end portions comprising hollow interiors terminating at end openings, the end portions being configured to removably receive portions of a suture segment; and
a staple drive coupled to the staple to impel the staple containing the suture segment into tissue and to retract the staple from the tissue while leaving the suture segment in the tissue.

2. The suturing system of Definition 1, wherein the staple drive comprises an impel trigger configured to initiate driving of the staple towards the tissue by the staple drive in response to contact of the impel trigger with the tissue.

3. The suturing system of Definition 2, wherein the impel trigger projects from a housing and is configured to initiate driving the staple toward the tissue by the staple drive in response to pressing of the impel trigger against the tissue to retract the impel trigger into the housing.

4. The suturing system of Definition 3, wherein the impel trigger comprises a staple guide further configured to guide movement of the staple towards the tissue.

5. The suturing system of Definition 4, wherein the staple guide comprises a funnel.

6. The suturing system of Definition 1 further comprising:
a housing;
a feed reel rotatably supported by the housing for supplying a carrier line supporting suture segments across the staple prior to impelling of the staple by the staple drive.

7. The suturing system of Definition 6 further comprising:
take-up reel rotatably supported by the housing for winding portions of the carrier line no longer supporting suture segments.

8. The suturing system of Definition 7 further comprising a line feeder, the line feeder comprising:
a series of ratchet teeth extending about the axis and supported by the take-up reel;
a pawl is biased into engagement with the series of ratchet teeth to inhibit rotation of the take-up reel; and
an impel trigger projecting from the housing and configured to rotate the take-up reel in response to pressing of the impel trigger against the tissue to retract the impel trigger into the housing.

9. The suturing system of Definition 7 comprising:
a housing rotatably supporting the take-up reel and the feed reel for rotation about an axis; and
a line feeder, the line feeder comprising:
a spring coupled to the housing and configured to rotate the take-up reel;
a series of ratchet teeth extending about the axis and supported by one of the housing and the take-up reel;
a catch supported by the other of the housing and the take-up reel, the catch and the ratchet teeth being resiliently biased into engagement to inhibit rotation of the take-up reel; and
an impel trigger projecting from the housing and configured to disengage the catch and permit rotation of the take-up reel by the spring in response to pressing of the impel trigger against the tissue to retract the impel trigger into the housing.

10. The suturing system of Definition 9, wherein the impel trigger comprises a wedge ramp configured to move the take-up reel away from the housing to disengage the catch and the series of ratchet teeth.

11. The suturing system of Definition 8, wherein the staple drive comprises:
a guide channel carried by the staple;
a first drive link pivotally supported by the housing, a first end rotatably and slidably received within the guide channel and a second end;
a second drive link pivotally supported by the housing a first end rotatably and slidably received within the guide channel and a second end; and
the impel trigger, wherein the impel trigger is operably coupled to the first drive link and the second drive link to pivot the first drive link and the second drive link to drive the staple towards the tissue in response to pressing of the impel trigger against the tissue to retract the impel trigger into the housing.

12. The suturing system of Definition 11, wherein the impel trigger is resiliently biased towards an extended state beyond the housing and wherein the staple is resiliently biased towards a retracted position within the housing.

13. A suture supply line comprising:
a carrier line; and
a series of suture segments carried by and separable from the carrier line.

14. The suture supply line of Definition 13, wherein each of the suture segments comprises a series of barbs.

15. The suture supply line of Definition 13, wherein each of the suture segments comprises:
a first series of barbs pointing in a first direction away from a center of the segment; and
a second series of pointing and a second direction away from the center of the segment.

16. The suture supply line of any of Definitions 13-16, wherein the carrier line is formed from a first material and wherein the series of suture segments are formed from a second material different than the first material.

17. The suture supply line of any of Definitions 13-16, wherein each of the suture segments is formed from an organ absorbable and dissolvable material.

18. The suture supply line of Definition 17, wherein the carrier line is formed from a non-organ absorbable and non-dissolvable material.

19. The suture supply line if any of Definitions 1-18, wherein each suture segment of the series of suture segments is connected to the carrier line by at least one breakable connector.

20. A suture segment comprising:

a flexible line having a first enlarged portion proximate a first end and a second enlarged portion proximate a second end.

21. The suture segment of Definition 20, wherein the first enlarged portion comprises a barb.

22. The suture segment of Definition 21, wherein the second enlarged portion comprises a second barb.

23. The suture segment of Definition 20, wherein the flexible line has a first plurality of barbs on a first side of and pointing away from a longitudinal center of the flexible line and a second plurality of barbs on a second side of and pointing away from the longitudinal center of the flexible line.

24. The suture segment of Definition 20, wherein the flexible line has shape memory.

25. The suture segment of Definition 20, wherein the flexible line is formed from an organ absorbable and dissolvable material.

26. A suturing system comprising:

a housing;

a staple pack movable between a retracted position within the housing and an extended position beyond the housing;

a bias resiliently biasing the staple pack to the retracted position;

a staple advance actuatable to move the staple pack against the bias to the extended position.

27. The suturing system of Definition 26 further comprising:

a pair of grippers movable between an open state and a closed state.

28. The suturing system of Definition 27, wherein the pair grippers are movable to the closed state automatically in response to pressing of the system against underlying tissue.

29. The suturing system of Definition 27, wherein the pair grippers are resiliently biased towards the open state.

30. The suturing system of Definition 27 further comprising a pressure foot movable between a raised position and a lowered position, the when the pressure foot extends beyond the housing so as to engage the underlying tissue prior to engagement of the underlying tissue by the housing and wherein the pressure foot is configured such that pressing of the pressure foot against the underlying tissue moves the pressure foot relative to the housing to move the grippers to the closed state.

31. The suturing system of Definition 26, wherein the staple pack comprises a series of staples, each of the staples releasably receiving a suture segment.

32. The suturing system of Definition 26, wherein the staple pack is removable from the housing.

Although the present disclosure has been described with reference to example implementations, workers skilled in the art will recognize that changes may be made in form and detail without departing from the scope of the claimed subject matter. For example, although different example implementations may have been described as including features providing benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A suturing system comprising:

a suturing device comprising:

a staple comprising a center portion and end portions extending from the center portion, the end portions comprising hollow interiors terminating at end openings, the end portions being configured to removably receive portions of a suture segment;

a second staple comprising a second center portion and second end portions extending from the second center portion, the second end portions comprising second hollow interiors terminating at second end openings, the second end portions being configured to removably receive portions of a second suture segment; and a staple drive coupled to the staple to impel the staple containing the suture segment into tissue and to retract the staple from the tissue while leaving the suture segment in the tissue, wherein the staple drive is coupled to the second staple to impel the second staple containing the second suture segment into the tissue and to retract the second staple from the tissue while leaving the second suture segment in the tissue.

2. The suturing system of claim 1, wherein the center portion has a hollow interior to removably receive portions of the suture segment.

3. The suturing system of claim 1, wherein the staple drive is configured to concurrently impel the staple and the second staple into the tissue and to concurrently retract the staple and the second staple from the tissue while concurrently leaving the suture segment and the second suture segment in the tissue.

4. The suturing system of claim 3, wherein the staple and the second staple extend in a first plane and a second plane oblique to the first plane.

5. The suturing system of claim 4, wherein the first plane and the second plane extend radially with respect to an intersect one another along a centerline.

6. The suturing system of claim 3, wherein the staple drive comprises:

a first slotted member coupled to the staple and having a first slot;

a second slotted member coupled to the second staple and having a second slot;

a first drive member slidably received within the first slot;

a second drive member slidably received within the second slot; and an actuation interface operably coupled to the first drive member and the second drive member, wherein movement of the actuation interface in a first direction concurrently moves the first drive member and the second drive member along the first slot and the second slot to impel the staple, respectively, into the tissue, and wherein movement of the actuation interface in a second direction concurrently moves the first drive member and the second drive member along the first slot and the second slot to retract the staple and the second staple, respectively, from the tissue.

7. The suturing system of claim 1, wherein the staple drive is configured to concurrently support a plurality of staples, including the staple, 360 degrees around a centerline and is configured to drive each of the plurality of staples into the tissue towards the centerline and retract each of the plurality of staples from the tissue, leaving a plurality of suture segments, including the suture segment, within the tissue.

8. The suturing system of claim 7, wherein the staple drive comprises:

a first slotted member coupled to the staple and having a first slot;

a second slotted member coupled to a second staple of the plurality of staples and having a second slot;

a first drive member slidably received within the first slot;

a second drive member slidably received within the second slot; and an actuation interface comprising a ring operably coupled to the first drive member and the second drive member, wherein movement of the ring in a first direction concurrently moves the first drive member and the second drive member along the first slot and the second slot to impel the staple and the second staple, respectively, into the tissue, and wherein movement of the ring in a second direction concurrently moves the first drive member and the second drive member along the first slot and the second slot to retract the staple and the second staple, respectively, from the tissue.

9. The suturing system of claim 7, wherein the staple drive comprises a first clamshell portion and a second clamshell portion that mate about the centerline.

10. The suturing system of claim 1, wherein the staple drive comprises:

a slotted member coupled to the staple and having a slot; and a drive member slidably received within the slot, wherein the slotted member and the drive member are configured such that movement of the drive member in a first direction along the slot impels the staple into the tissue and movement of the drive member and a second direction along the slot retract the staple from the tissue.

11. The suturing system of claim 1 further comprising the suture segment.

12. The suturing system of claim 11, wherein the suture segment comprises a flexible line having a first enlarged portion proximate a first end and a second enlarged portion proximate a second end.

13. The suturing system of claim 12, wherein the first enlarged portion comprises a barb.

14. The suturing system of claim 13, wherein the second enlarged portion comprises a second barb.

15. The suturing system of claim 11, wherein the suture segment has shape memory.

16. The suturing system of claim 11, wherein the suture segment is formed from an organ absorbable and dissolvable material.

17. The suturing system of claim 11, wherein the suture segment comprises at least three spaced barbs along its length.

18. The suturing system of claim 1, wherein the staple drive comprises an impel trigger configured to initiate driving of the staple towards the tissue by the staple drive in response to contact of the impel trigger with the tissue.

19. A suturing system comprising:

a suturing device comprising:

a staple comprising a center portion and end portions extending from the center portion, the end portions comprising hollow interiors terminating at end openings, the end portions being configured to removably receive portions of a suture segment; and a staple drive coupled to the staple to impel the staple containing the suture segment into tissue and to retract the staple from the tissue while leaving the suture segment in the tissue, wherein the staple drive is configured to concurrently support a plurality of staples, including the staple, 360 degrees around a centerline and is configured to concurrently drive each of the plurality of staples into the tissue towards the centerline and concurrently retract each of the plurality of staples from the tissue, leaving a plurality of suture segments, including the suture segment, within the tissue.

* * * * *